(12) United States Patent
Hansen et al.

(10) Patent No.: US 7,116,407 B2
(45) Date of Patent: *Oct. 3, 2006

(54) SYSTEM FOR AXIAL PATTERN ANALYSIS OF MULTICELLULAR ORGANISMS

(75) Inventors: W. Peter Hansen, Canaan, NY (US); Anthony A. Ferrante, Belmont, MA (US); Russell J. Gershman, Burlington, MA (US); Petra B. Krauledat, Canaan, NY (US); Donald F. Perrault, Jr., Brighton, MA (US)

(73) Assignee: Union Biometrica, Inc., Holliston, MA (US)

( * ) Notice: Subject to any disclaimer, the term of this patent is extended or adjusted under 35 U.S.C. 154(b) by 251 days.

This patent is subject to a terminal disclaimer.

(21) Appl. No.: 10/076,363

(22) Filed: Feb. 15, 2002

(65) Prior Publication Data

US 2002/0176069 A1  Nov. 28, 2002

Related U.S. Application Data

(63) Continuation-in-part of application No. 09/932,413, filed on Aug. 17, 2001, now abandoned, and a continuation-in-part of application No. 09/465,215, filed on Dec. 15, 1999, now abandoned.

(60) Provisional application No. 60/226,701, filed on Aug. 18, 2000, provisional application No. 60/112,280, filed on Dec. 15, 1998.

(51) Int. Cl.
*G01N 21/00* (2006.01)
*G01N 33/553* (2006.01)
*B07C 5/36* (2006.01)

(52) U.S. Cl. .......................... 356/73; 356/36; 209/639; 436/525; 435/320.1

(58) Field of Classification Search ............ 356/72–73, 356/625, 635, 36–42, 246, 237.1; 209/639; 435/29, 26, 320.1; 436/525

See application file for complete search history.

(56) References Cited

U.S. PATENT DOCUMENTS

4,110,043 A  8/1978  Eisert .................... 356/102
4,284,412 A  8/1981  Hansen et al.
(Continued)

FOREIGN PATENT DOCUMENTS

EP    1 159 600 A    12/2001
WO   WO 99/37814    7/1999

(Continued)

OTHER PUBLICATIONS

International Search Report issued for corresponding PCT application PCT/US02/26334.

(Continued)

*Primary Examiner*—Gregory J. Toatley, Jr.
*Assistant Examiner*—Sang H. Nguyen
(74) *Attorney, Agent, or Firm*—Choate, Hall & Stewart, LLP; Brenda Herschbach Jarrett; Stacy L. Blasberg

(57) ABSTRACT

A method of using elongate multicellular organisms in conjunction with a specialized flow cytometer for drug discovery and compound screening. A stable, optically detectable linear marker pattern on each organism is used to construct a longitudinal map of each organism as it passes through the analysis region of the flow cytometer. This pattern is used to limit complex data analysis to particular regions of each organism thereby simplifying and speeding analysis. The longitudinal marker pattern can be used to alter signal detection modes at known regions of the organism to enhance sensitivity and overall detection effectiveness. A repeating pattern can also be used to add a synchronous element to data analysis. The marker patterns are established using known methods of molecular biology to express various indicator molecules. Inherent features of the organism can be rendered detectable to serve as marker patterns.

14 Claims, 18 Drawing Sheets

U.S. PATENT DOCUMENTS

| | | | | |
|---|---|---|---|---|
| 4,765,737 | A | | 8/1988 | Harris et al. ................. 356/336 |
| 5,180,065 | A | * | 1/1993 | Touge et al. ................. 209/577 |
| 5,578,460 | A | * | 11/1996 | Ebersole et al. .............. 435/29 |
| 5,668,112 | A | * | 9/1997 | Lipsky et al. .................. 514/19 |
| 5,798,222 | A | * | 8/1998 | Goix ........................... 435/29 |
| 5,804,384 | A | * | 9/1998 | Muller et al. ................... 435/6 |
| 6,156,502 | A | * | 12/2000 | Beattie .......................... 435/6 |
| 6,400,453 | B1 | * | 6/2002 | Hansen .................... 356/237.1 |
| 6,657,713 | B1 | | 12/2003 | Hanson .................... 356/237.1 |
| 2002/0142288 | A1 | | 10/2002 | Kaultkiewicz et al. ......... 435/4 |
| 2002/0176069 | A1 | | 11/2002 | Hansen et al. |

FOREIGN PATENT DOCUMENTS

| | | |
|---|---|---|
| WO | WO 00/11449 | 3/2000 |
| WO | WO 00/36396 | 6/2000 |
| WO | WO 01/48455 | 7/2001 |
| WO | WO 03/16875 | 2/2003 |
| WO | WO 03/021272 | 3/2003 |
| WO | WO 02/066960 | 11/2003 |

OTHER PUBLICATIONS

U.S. Appl. No. 09/378,634, Hansen, Pending.

U.S. Appl. No. 09/465,215, Hansen, Pending.

Burdine, et al., "egl-17 encodes an invertebrate fibroblast growth factor family member required specifically for sex myoblast migration in *Caenorhabditis elegans*," Proc. Natl. Acad. Sci., U.S.A. 94:2433-2437.

Burdine, et al., "EGL-17(FGF) expression coordinates the attraction of the migrating sex myoblasts with vulval induction in *C. elegans*," Development 125:1083-1093.

Byerly, L., RC. Cassada and RL. Russell. Machine for rapidly counting and measuring the size of small nematodes. Rev Sci Instrum. May 1975; 46(5):517-22.

Dubelaar, G.B., A.C. Groenwegen, W. Stokdijk, G.J. van den Engh, and J.W. Visser, "Optical Plankton Analyser: a Flow Cytometer for Plankton Analysis, II: Specifications", Cytometry Sep. 10, 1989 (5): 529-539.

Harris, J., Honigberg, L., Robinson, N., and Kenyon, C. (1996). Neuronal cell migration in *C. elegans*: regulation of Hox gene expression and cell position. Development, 122, 3117-31.

Kenyon, C. (1986). A gene involved in the development of the posterior body region of *C. elegans*. Cell, 46, 477-487.

Korswagen, H. C., Herman, M. A., and Clevers, H. C. (2000). Specificity of β-catenin signalling in *C. elegans*. Nature,406 (Aug. 3, 2000): 527-532.

Lejeune et al., (1995) Wnta cloning, expression and up-regulation in human primary breast cancers Clin. Cancer Res. 1: 215-222.

Morin, P. J., Sparks, A. B., Korinek, V., Barker, N., Clevers, H., Vogelstein, B., and Kinzler, K. W. (1997). Activation of beta-catenin-Tcf signaling in colon cancer by mutations in beta-catenin or APC. Science, 275, 1787-90.

Nusse, R., and Varmus, H. E. (1982). Many tumors induced by the mouse mammary tumor virus contain a provirus integrated in the same region of the host genome. Cell, 31, 99-109.

Peeters, J.C., G.B. Dubelaar, J. Ringelberg, and J.W. Visser, "Optical Plankton Analyser: a Flow Cytometer for Plankton Analysis, I: Design Considerations" Cytometry Sep. 10, 1989 (5): 522-528.

Rubinfeld, B., Robbins, P., El-Gamil, M., Albert, I., Porfiri, E., and Polakis, P. (1997). Stabilization of beta-catenin by genetic defects in melanoma cell lines. Science, 275, 1790-2.

Salser, S.-J., and Kenyon, C. (1992). Activation of a *C. elegans Antennapedia* homologue in migrating cells controls their direction of migration. Nature, 355, 255-8.

Tsien, R. Rosy Down for Fluorescent Proteins. Nature Biotechnology (1999) 17: 956-57.

\* cited by examiner

SYSTEM FOR AXIAL PATTERN ANALYSIS OF MULTICELLULAR ORGANISMS

PRIORITY INFORMATION

This application is a continuation-in-part of U.S. application Ser. No. 09/932,413, filed Aug. 17, 2001 now abandoned, which claims priority to U.S. Provisional Application No. 60/226,701, filed Aug. 18, 2000. This application is also a continuation in part of U.S. application Ser. No. 09/465,215, filed Dec. 15, 1999 now abandoned, which claims priority to U.S. Provisional Application No. 60/112,280, filed Dec. 15, 1998. Each of the above-referenced applications is incorporated herein by reference.

FIELD OF THE INVENTION

This invention concerns the field of automated analysis of complex, multicellular model organisms that are particularly useful in the field of drug discovery, of toxicology, and development.

BACKGROUND OF THE INVENTION

Rapid, high-throughput compound screening assays have revolutionized the field of drug discovery. Automated drug discovery assays measure changes in a variety of biochemical pathways in vitro. For example, microarray assays simultaneously assess the effect of thousands of compounds on a particular biochemical pathway in vitro. However, such automated drug screening assays are not readily available for assessing the in vivo effects of multiple compounds on complex multicellular organisms. In particular, assessing the effect of one or more compounds on the development or physiology of a multicellular organism remains a tedious manual task requiring hundreds of hours of labor by highly skilled technicians.

Intact multicellular organisms, such as the nematode *Caenorhabditis elegans*, the fruit fly *Drosophila melanogaster*, or the zebrafish *Danio rerio* are frequently used as model systems to help understand the function of human genes that have been implicated in disease. Human gene homologs are often identified in these model organisms and provide valuable tools for studying the biological function of the genes in vivo. Such mutations frequently result in an easily observable phenotypic change in the model organism. Furthermore, it has been shown that certain pharmacological compounds collaterally produce optically detectable changes in these mutant organisms. These changes can be used to identify specific compounds that interact with a particular gene product in vivo. The addition of such functional genomic techniques to the repertoire of molecular biology and biochemistry methods can greatly accelerate the drug discovery process.

Mutants of intact organisms are used as a new class of methods for in vivo drug screening of libraries of potential pharmacological compound produced through the use of combinatorial chemical methods. With these organisms, one can identify targets for drug intervention without the need to completely understand the complex biochemical pathways that relate the genome to the phenotype. In addition, investigators can annotate drug libraries for toxicity, non-specific activity, or cell membrane permeability by observing their behavior in intact organisms. In this way, toxic or ineffective libraries and/or library members can be discarded at an early stage of testing without wasting valuable resources. This allows rapid and economical screenings of the compound libraries for new and useful therapeutic compounds, while limiting politically controversial testing on mammals.

While model organisms such as *C. elegans*, *D. melanogaster*, and *D. rerio* have been proven useful in the study of human disease, they have not yet been successfully used in the field of high speed, high throughput drug discovery. This presents a significant hindrance to investigators that need to search through thousands of multicellular organisms for the phenotype of a new mutation or for a response to a panel of sample drugs. For example, with today's molecular biology techniques, a large laboratory can produce deletion mutations in a multicellular test organism at a rate of 20 to 30 per month. In order to evaluate the effect of each member of a chemical compound library (that frequently contains 100,000 discrete compounds) on a single deletion mutant, one must manually manipulate and deposit a precise number of organisms of the mutant strain at the same developmental stage into various containers, such as wells of a microtiter plate array. Wild-type or deviants from the desired mutant strain, or organisms at a different development stage must be eliminated. The use of such slow, manual methods for the selection and deposition of organisms of the proper type greatly delays the entire process of drug discovery. Moreover, manual methods rely on pipettes that dispense accurate volumes of fluid but not accurate numbers of organisms. In many studies, where reproduction rate is altered by the mutation, it is necessary to begin with an exact and known number of multicellular organisms in each well. This is, at best, a daunting requirement.

The effect of a therapeutic compound or toxic environment on the mutant strain or expression system can be determined by identifying changes in the spatial pattern of fluorescence or staining. Fluorescent protein genes are typically used as reporters for gene expression in a wide variety of organisms (Tsien, R. *Nature Biotechnology* (1999) 17: 956–57). For example, green fluorescent protein (GFP) is used as a reporter gene to indicate that an inserted gene has been expressed. The expression of the fluorescent protein usually occurs in a specific spatial pattern within a multicellular organism. Discrimination of one pattern from another is currently carried out manually using a fluorescent microscope. Like the selection and deposition step, this is an extremely tedious task requiring a significant number of workers that are trained at high academic levels.

Prior art methods of selecting multicellular organisms have relied on instruments that performed a "slit-scan" of whole organisms as they passed through the analysis zone of a laser. Methods of detecting fine detail in slit-scanning have relied on apparatuses that utilize diffraction limited optics to create narrow line focus and image plane masks to act as optical spatial filters. This narrow line of focus is sufficient for analyzing single cells, but is insufficient for detecting and spatially locating a particular feature against the more complex background profile of light scatter and autofluorescence presented by a multicellular organism. For example, the diameter of a mature *C. elegans* is approximately 70 micrometers. This means that the background autofluorescence from a nematode is approximately ten times that from a white blood cell (about seven micrometers in diameter), while a fluorescence reporter signal from a single *C. elegans* cell is no greater than that from a single blood cell. In the case of *D. melanogaster* (fruit fly) larvae, the situation is even worse because the diameter of an advanced stage larva is of the order of one millimeter, which means that autofluorescence is much more than a hundred times greater than in single blood cells. This means that experimentally created, fluorescent features along the axis of a multicellular organism may produce a much weaker optical signal than the autofluorescence background. One can imagine that an axial profile of auto fluorescence with very high peaks and valleys would effectively mask an experimentally created fluorescence feature.

Flow instruments have been used to count the number of nematodes in a fluid volume. Such a device was described by Byerly et al (Byerly,et al., *Rev. Sci. Instrum.* (1975) May 46(5): 517-22), where a flow cytometer employed sheath flow to orient nematodes along the direction of flow so that their size could be measured and organism-by-organism counts could be made by an electrical impedance method. The device was similar to a commercial Coulter counter. The use of the impedance sensor, which can only estimate overall size, and cannot spatially resolve localized features along the major axis of the organism limits the Byerly et al. instrument. In addition to this limitation, the Byerly et al. instrument could not select and deposit (sort) specific organisms.

U.S. Pat. Ser. No. 6,400,453 issued Jun. 6, 2002, which is incorporated herein by reference, describes an instrumentation system for the rapid analysis and sorting of multicellular organisms using optical characteristics such as light scatter and fluorescence to classify each organism in a flowing stream. A single value of fluorescence intensity at a given emission wavelength is detected and assigned to each organism. However, this instrument reports only the intensity, not the position of fluorescence along the major (long) axis of the organisms.

An optical flow instrument for analyzing elongate organisms such as plankton with widths of 500 μm and lengths over 1000 μm has also been described with sheath flow to achieve orientation of the plankton. (J. C. Peters, G. B. Dubelaar, J. Ringelberg, and J. W. Visser, "Optical Plankton Analyser: a Flow Cytometer for Plankton Analysis, I: Design Considerations" Cytometry Sep. 10, 1989 (5): 522–528; and G. B. Dubelaar, A. C. Groenwegen, W. Stokdijk, G. J. van den Engh, and J. W. Visser, "Optical Plankton Analyser: a Flow Cytometer for Plankton Analysis, II: Specifications", Cytometry Sep. 10, 1989 (5): 529–539). The size range of the plankton used in these optical flow cytometers is similar to that encountered with *C. elegans* nematodes, fruit fly larvae, and zebrafish embryos; however, there is no provision that avoids the ambiguous light scatter signals that are eliminated by the present invention.

There exists the need for a high-speed system for automatically identifying and physically selecting multicellular organisms with certain spatially distinct, optically detectable, phenotypic characteristics from mixed populations. Such a system must have the ability to locate and measure the intensity and position of experimentally created optical features in the presence of overwhelming autofluorescence.

SUMMARY OF THE INVENTION

The present invention provides a system for identifying and physically selecting multicellular organisms from mixed populations on the basis of spatially distinct, optically detectable, phenotypic characteristics. Two key components of this system include the use of fluorescence markers to provide positional and orientational information about model multicellular organisms. According to certain aspects of the invention, strains of model multicellular organisms are generated that have a first marker pattern feature that is spatially consistent and is used to orient the organisms along their major axes. In preferred embodiments, the strains of model organisms also include a second inducible or modifiable feature whose position may be determined in relation to the first marker pattern features. For example, strains of organisms may be generated that include fluorescent marker proteins in one or more particular cells or physiological locations (e.g., the head and the tail) in the organisms. The strains of model organisms may also include a second feature that is inducible by a particular signal, e.g., a genetic mutation. The multicellular organisms of the invention are particularly useful for high-throughput drug screening assays wherein the organisms are exposed to compounds from a combinatorial chemical compound library and assessed for the presence of the particular second feature.

A second key component of the invention is the development of novel flow cytometry and sorting instrumentation for generating spatial profiles of the model multicellular organisms, which preferably contain the spatially distinct, optically detectable, phenotypic characteristics described herein, by measuring fluorescent and light scattering properties. The model organisms are analyzed and sorted based on spatial profile optical measurements. The technical details of the optical, electronic, and fluidic components of the instrumentation and algorithms of the invention, are described herein.

The present invention further provides two distinct methods of optically detecting an organism in the detector beam of the inventive flow cytometer device. The difference between the methods hinges on the type of second signal used to gate the fluorescence signals on the organisms so that they may be detected over background autofluorescence and noise signals. In one preferred embodiment, light scattered in the forward direction by the organism is used to generate the gate signal for fluorescence detection. In another preferred embodiment, light attenuated by the organism in the forward direction is used to generate a gate signal for fluorescence detection.

Experimental data is provided that demonstrates use of the inventive instrument to screen and sort the model organisms having spatially distinct, optically detectable, phenotypic characteristics. This data illustrates the elegant nature of the invention, which combines the use of multicellular organisms having spatially distinct, optically detectable, phenotypic characteristics with an instrument that can analyze this information and use it to sort the multicellular organisms base on specific spatially distinct features.

BRIEF DESCRIPTION OF THE DRAWINGS

The invention is described with reference to the several figures of the drawing, as follows.

DETAILED DESCRIPTION OF THE INVENTION

Figure 1:
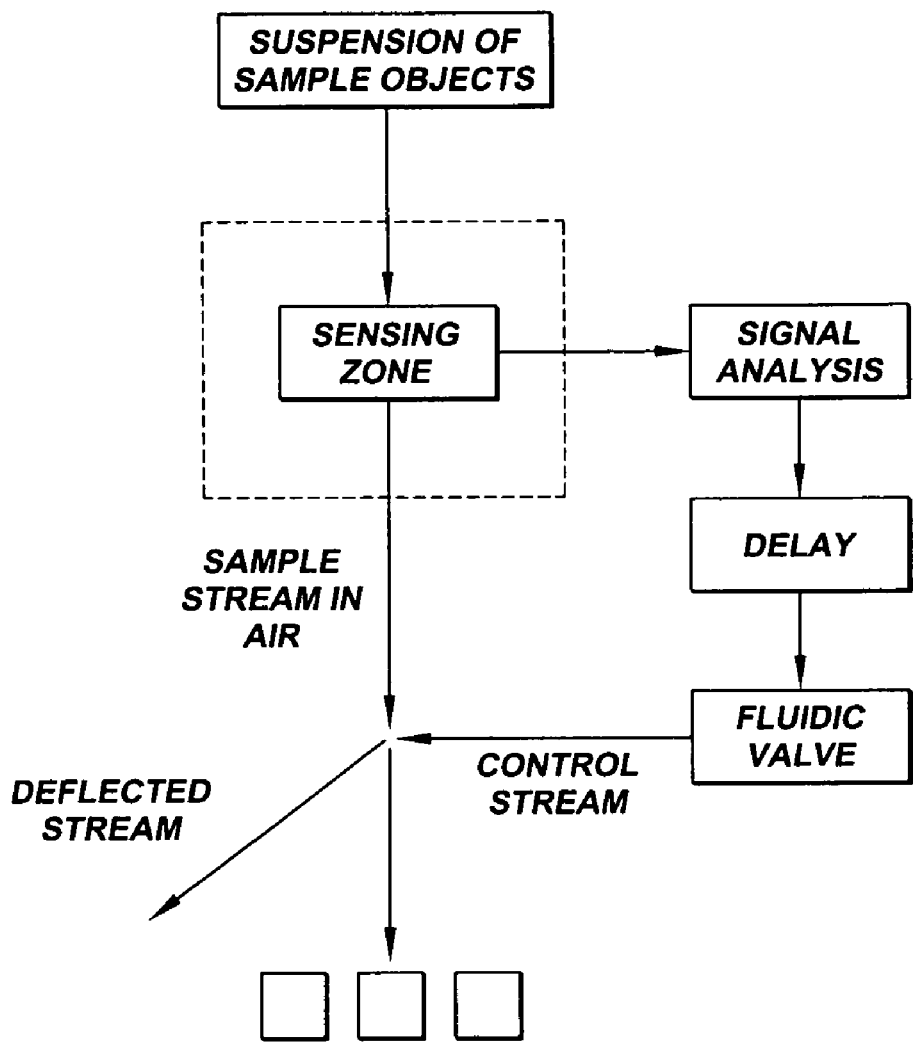
FIG. 1 shows a diagrammatic representation of optics, flow cell, command electronics, and fluid switch.

Drug screening assays generally focus on a single step of an often complex biochemical pathway. A compound that affects the biochemical pathway is generally identified as a "hit." Assays can be designed in complex, living, multicellular organisms such that a compound that affects any component of a biochemical pathway is identified as a "hit". Use of a complex, multicellular organism can provide data relating to the toxicity and the impact of a compound on specific biochemical events. The present invention provides, for the first time, an automated system for identifying and physically selecting multicellular organisms from mixed populations on the basis of spatially distinct, optically detectable, phenotypic characteristics.

By including both an instrument, namely a flow analyzer and sorter, and a population of organisms with marker pattern features, the system of the present invention allows one to localize and report not only the intensity of fluorescence on an organism, but also the position of fluorescence along the major (long) axis of an organism. The inventive automated system, generating new spatial information can be used to separate (sort) mutants organisms with a particular phenotypic trait from a mixed population of organisms. In certain preferred embodiments, the particular phenotypic trait can result from contact of the organism with a compound. In other preferred embodiments, the particular phenotypic trait results from genetically crossing two genotypically different multicellular organisms. Alternatively, the automated system of the present invention can be used to separate multicellular organisms that are at a particular stage of development. Examples of applicable multicellular organisms are all stages developmental of *Caenorhabditis elegans, Drosophila melanogaster* (fruit fly) larvae and embryos, or *Danio rerio* (zebrafish) embryos, which are useful as model organisms for human disease and functional genomics studies. According to certain preferred embodiments, organisms, such as nematodes, having markers at every stage of development can be generated for use in the present invention.

The inventive system, which combines strains of multicellular organisms characterized by a stable spatial pattern of fluorescence, staining, or other optically detectable characteristics, with an instrument that can accurately sort multicellular organisms based on the position of an experimental feature relative to other invariant features by axial scanning, greatly benefits the areas of developmental biology and drug discovery. As pointed out above, multicellular organisms are frequently used as models for human disease and provide excellent tools for testing the effect of a test compound on a particular biochemical pathway in vivo.

For example, the effect of a therapeutic compound or toxic environment in vivo can be determined by monitoring changes in the spatial patterns of selected features on the multicellular organisms. For example, in analyzing the effects of a drug screen on a particular feature, it would be desirable to know if the feature was present or absent, or up-regulated or down-regulated. As but another example, locating spatial features on a multicellular organism is important for understanding development and differentiation of structures during the organism's life cycle. Using the system of the present invention, one could also tag a cell for abnormal cell migration. One could examine a particular in vivo function, e.g., axon growth (e.g., by measuring the length of an axon by labeling the axon cell with a fluorescent marker) and determine whether reversing the mutation causes the nerve to grow to a normal length.

Automating the detection of spatial patterns of signals further improves the objectivity and speed of analysis. The present invention provides the first system that is suitable for the high-speed analysis and placement of axial features within transparent, or partially transparent, multicellular organisms. The components of this unique system, including the multicellular organisms and the instrument, are discussed in detail below.

Fluorescent Markers for Spatial Analysis

Figure 9A:
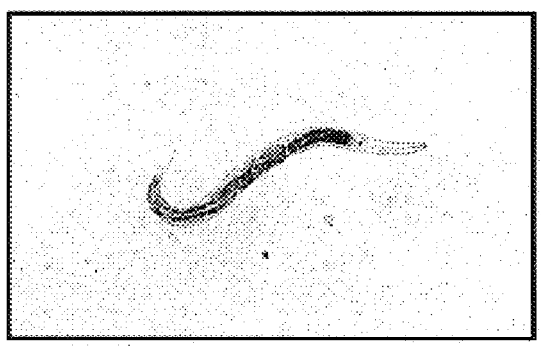
FIG. 9 shows a series of photomicrographs of transgenic *C. elegans* expressing ZsYellow under the control of the egl-17 promoter with panel A showing a white light image with the corresponding fluorescence image shown in panel C; panel B similarly corresponds to the fluorescence image of panel D.
Figure 9B:
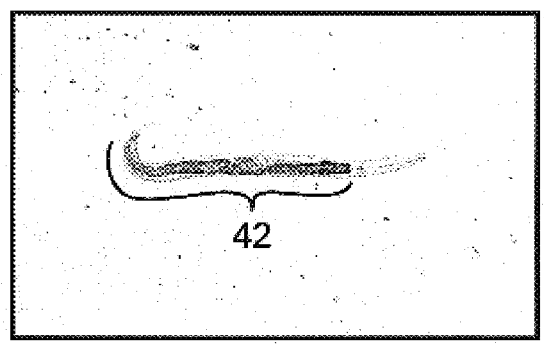
Figure 9C:
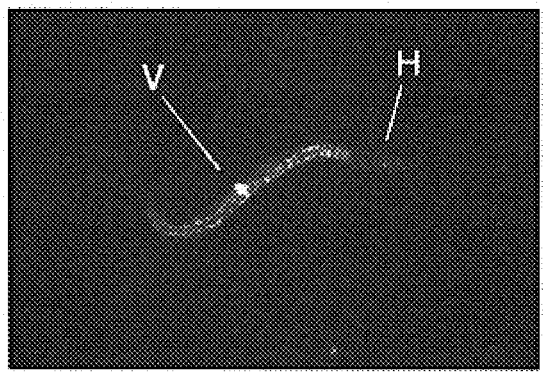
Figure 9D:
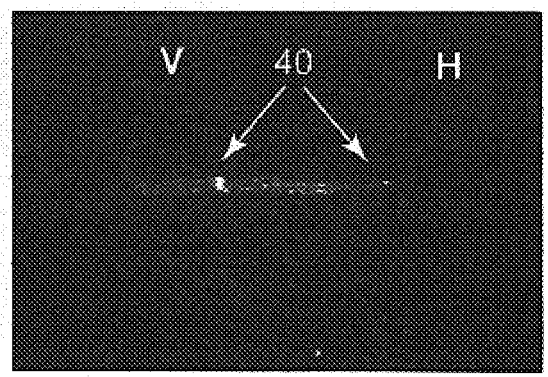

As shown in FIG. 9B, in one embodiment of the system, the present invention includes a population of multicellular organisms having a plurality of spatially distinct, optically detectable, phenotypic characteristics 40 and an instrument for detecting such characteristics. According to the present invention, a spatially distinct, optically detectable, phenotypic characteristics 40 includes a marker pattern 42 of spatially consistent features that can be used to orient the organism along its major axis. The spatially distinct, optically detectable, phenotypic characteristics 40 may also include a second feature that is modifiable or inducible when the population is subjected to a test treatment. Test treatments include exposure to a chemical compound (e.g., a chemical compound from a complex chemical compound library), a harsh environment (e.g., starvation, increased temperature, decreased temperature, overcrowding, changes in light, etc.), a mutagenesis procedure (e.g., exposure to a known chemical mutagen), a genetic crossing procedure (e.g., where two strains of organisms are crossed to determine how particular phenotypic traits or biochemical pathways interact), etc.

Those skilled in the art will recognize that any spatially distinct, optically detectable, phenotypic characteristics may be used to orient an organism along its major axis. In certain preferred embodiments, the organism is aligned using only the first marker pattern of spatially consistent features and does not utilize the second feature induced by the test treatment, e.g., if one were to merely separate organisms with a particular set of first features.

The present invention further provides methods for sorting multicellular organisms based on a particular phenotype. A population is provided wherein each member of the population displays a marker pattern of spatially distinct features that can be used to orient the organism in the detection instrument and a second feature, whose presence and location is used to identify how the organism is to be sorted. Members of the population of organisms that display the second feature at the proper intensity or location with respect to the features of the marker pattern is separated from the members of the mixed population that do not have the second feature. The arrangement of the second feature with respect to the features of the marker pattern is a key to the ability to sort the organisms based on specific phenotypic traits.

For example, multicellular organisms can be sorted by first providing a population of test organisms having any combination of marker pattern features and second features; measuring the arrangement of the marker pattern features and the second features; and depositing members of the population based on the arrangement of the second feature with respect to the marker pattern features.

In certain preferred embodiments, a plurality of spatially distinct, optically detectable, phenotypic characteristics includes, in addition to the marker pattern of spatially consistent features and the second feature that is modifiable or inducible, multiple second features that are modifiable or inducible. Features could range in size from 10 micrometers to the full length of the organism. The arrangement of the multiple second features with respect to the marker pattern of features can be used to further characterize and sort certain members of the population based on multiple phenotypic characteristics. For example, an organism may have a plurality of mutations resulting from a mutagenesis procedure that are detectable by the instrument, and can be used to separate the organisms from the mixed population.

In certain preferred embodiments, members of the population are passed through the instrument and sorted based on the arrangement of the marker pattern features with respect to the one or more second features. Examples of features that can be classified as spatially distinct, optical characteristics include: the localized expression of DNA encoded fluorescent protein molecules, localized variations of the index of refraction or granularity, and localized variations in specific binding sites (receptors) for optically labeled antibodies, lectins, or other specific ligands. More specific features include the location of specific cells at particular developmental stages or the presence or absence of particular gene products at particular developmental stages, which can each be marked by the presence or absent of a fluorescent protein molecule.

Fluorescent protein genes have been used as reporters for gene expression in a wide variety of organisms (Tsien, R., *Nature Biotechnology* (1999)17: 956-57). The present invention permanently incorporates fluorescent proteins into large populations of multicellular organisms to create spatially marked strains that can be used in combination with a high-speed flow cytometer to detect and map the spatial location of other, experimentally generated second features, e.g., gene expression with a high degree of precision. The marker patterns serve as guides to focus and synchronize the signal processing and computational electronics on specific spatial regions of the experimental organism where expression is expected, thus improving processing speed and accuracy in the marked strain thus providing clues about the developmental aspects of the expression event.

Instrument

The present invention uses a fluid flow stream to orient elongate, multicellular, organisms and a narrowly focused, stationary, optical beam to scan them along their major axis as they flow. Features such as cell density, refractility, granularity, and fluorescence can be detected and recorded as a function of position along the length of the oriented organism (i.e., an axial pattern scan). The invention is an improvement in speed and statistical precision over current manual techniques for analyzing multicellular organisms one by one under the microscope. The information from the scan can be used to characterize gene expression and enable physical selection and deposition of phenotypes with desired characteristics, or it can be used to determine alterations in gene expression caused by toxic or therapeutic compounds.

Figure 15:
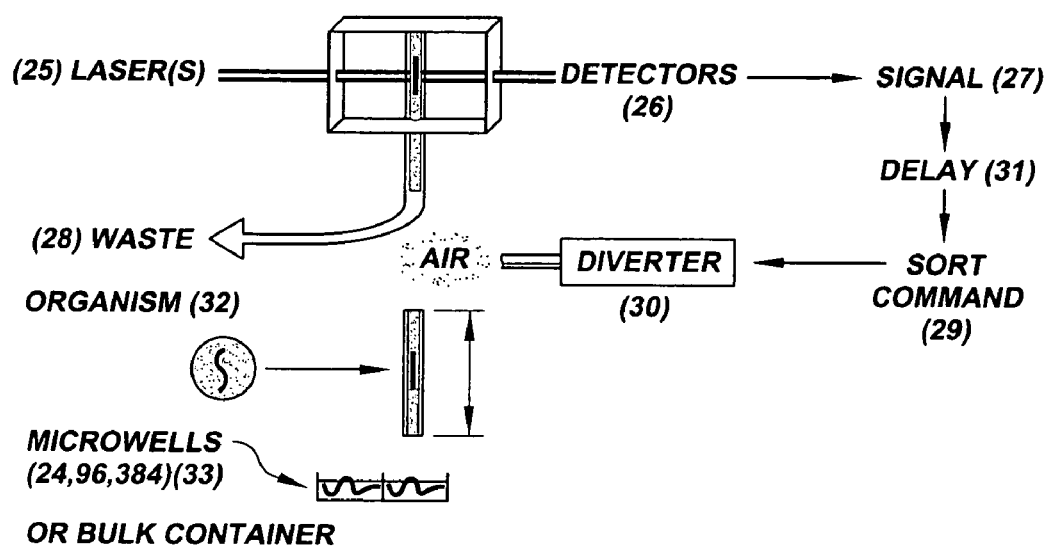
FIG. 15 illustrates the basic concept of the inventive sorting device where organisms that do not display a desired spatially distinct, optically detectable, phenotypic characteristic are separated from the organisms that do have a desired spatially distinct, optically detectable, phenotypic characteristic.

The basic components of the invention are shown in FIG. 15. Multicellular organisms are passed serially between a beam generated from a laser (25) and a detector (26). It is an important characteristic of the invention that the organisms are flowing at a constant velocity. For a given set of operating conditions it is possible to determine the amount of time required for an organism to travel from the laser beam to the diverter valve. That time is referred to as the delay. It is adjustable by the operator and typically is between 7 and 9 milliseconds. The passage of the organism through the laser beam causes a signal (27) to be produced, which is analyzed to determine the physical and optical characteristics of the organism including, but not limited to, its size (extinction and time of flight), overall fluorescence characteristics, and the location of fluorescence or light scatter features along the longitudinal axis of the organism. Typically the diverter valve is open so that all of the fluid exiting the flow cell is diverted to waste (28). Depending on the analysis, if the organism displays all of the desired sort parameters, a sort command (29) is generated and the diverter (30) valve is turned off at a time equal to the delay (31) described above. The desired organisms (32), having a desired second feature or other spatially distinct, optically detectable, phenotypic characteristics, fall directly into a bulk container or microwells (e.g., 24, 96, or 384 microwell plates) (33).

Optical System

The present invention provides an improved instrument that uses light scatter and fluorescence means to optically identify and activate fluidic sorting of multicellular organisms from live populations of organisms such as various life cycle stages of *Caenorhabditis elegans*, the larval stages of *Drosophila melanogaster*, and the embryonic stages of *Danio rerio*. In the case where fluorescence from these organisms is very weak, comparatively high levels of electronic noise accompany the electronic signals that are generated by the fluorescence detector and its associated circuitry. Because these weak signals cannot be used to mark the presence of an organism, another, less noisy, (second) signal must be used to gate fluorescence detection.

Two optical detection methods can be used to generate a low noise "gate" signal. The first method uses a light scatter signal from the organism which is collected over an acceptance angle of at least 20 degrees, preferably 20–90 degrees. Light scatter within a collection angle less than 20 degrees is rejected with the use of a spatial filter. Such a light scatter signal unambiguously gates even weak fluorescence signals. These signals can then be correlated with position along the major axis of elongate, multicellular organisms and used as enhanced analysis and sorting parameters. The second optical detection method by which the instrument of the present invention optically identifies and activates fluidic sorting of multicellular organisms from live populations of organisms is by using "extinction." This method utilizes the attenuation of the light entering the detector to signal that a worm has entered the light beam and the return of light entering the detector to signal that a worm has exited the light beam. Instead of light scatter, the attenuation of light with in a collection angle from 0 to 0.5–6.0 degrees in the horizontal axis, and less than 20 degrees in the vertical axis from the laser beam is used as a gating signal to indicate when the elongate multicellular organism is in the beam.

Without limiting the invention, we propose that when an organism intersects the laser beam, light is refracted and diffracted by the organism and thereby the light is radiated forward in an angular distribution pattern. The light attenuated by the organism at the focus point of the beam in a narrow angle around the axis is referred to as extinguished light, whereas light radiated in a wide angle relative to the optical axis is referred to as scattered light. The detected light distribution pattern may vary depending on the distance of the detector from the beam. If the distance between the organism and the detector is not set appropriately, the detector reads in-between the two regions so that the detector incorrectly measures the presence of an organism. According to the present invention, in the first optical detection method the distance between the organism passing through the beam and the detector is set so that the light scattered by the organism is collected, and light extinguished from the organism is rejected. In the second optical detection method light scattered by the organism is rejected, and light extinguished from the organism is collected.

Fluorescence: Excitation and Emission Optics

Fluorescence is captured at a 90-degree angle to the beam using a fluorescence collection lens. The collected light is transmitted through a series of dichroic mirrors such that different wavelengths are directed to three different photomultiplier detectors. The scattered excitation light, and unwanted fluorescence incident on the photomultiplier tubes are further attenuated using bandpass filters. Any combination of bandpass filters and dichroic mirrors can be used to spectrally resolved the fluorescence signal. However, the standard emission filters are optimized for detection of green, yellow, and red fluorescent proteins and stains (see FIG. 14).

Figure 14:
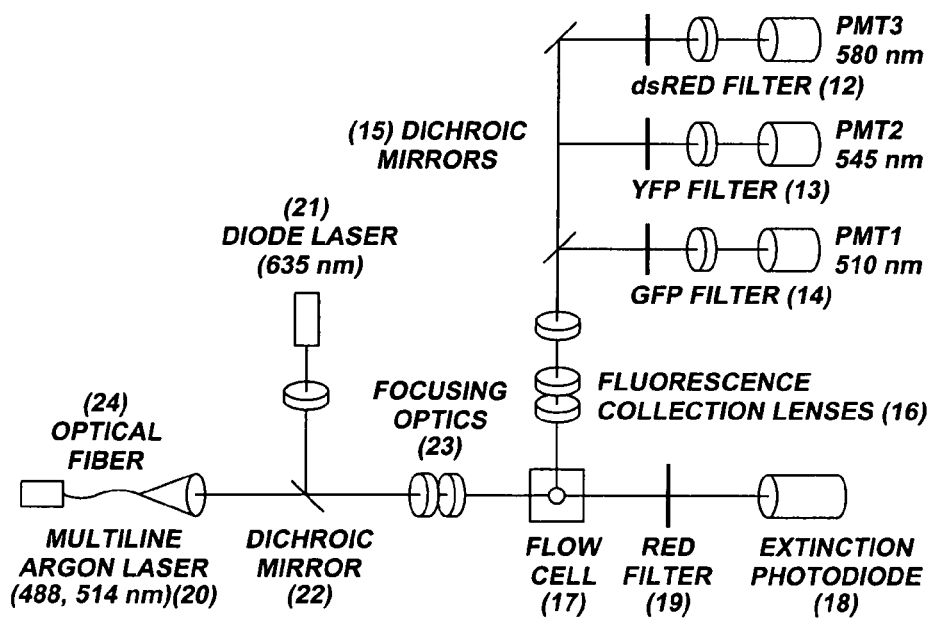
FIG. 14 illustrates the arrangement of the standard emissions filters in the inventive sorting device.

FIG. 14 illustrates the fluorescence optical excitation and detection optics configuration. The illumination/excitation laser (20) can be coupled to the optical assembly through an optical fiber. The light is then focused to a line within the flow cell (17) with beam formation optics (23). Light scatter measurements are made with a detector and spatial filters positioned in the laser beam path at the optical exit of the flow cell. A collection lens (16) used to collect the fluorescence at a 90 degree angle to the excitation illumination beam, and images the fluorescent light through a series of dichroics mirrors dichroic mirrors (15), and bandpass filters (12, 13, 14) onto a series photomultiplier tube (PMT) detectors. The intersection of the beam, organism and the collection lenses is called the analysis zone (8).

Gating Using Light Scatter: Optical Illumination/Detection Using Forward Scatter In the case where fluorescence from these organisms is very weak, comparatively high levels of electronic noise accompany the electronic signals that are generated by the fluorescence detector and its associated circuitry. These weak signals cannot be used to mark the presence of an organism, and another, less noisy, signal must be used to gate fluorescence detection. Axial light loss might be used as such a gate. Another preferred gate can be derived from the low-noise light scatter signal from the organism. Conventional light scatter gating, such as is practiced in flow cytometry of single cells, creates ambiguous signals when used on multicellular organisms and thus leads to false gating of fluorescence. A light scatter detection means and an extinction means is herein described which unambiguously gates these fluorescence signals. These signals can then be correlated with position along the major axis of elongate, multicellular organisms and used as enhanced analysis and sorting parameters.

Traditional optical flow cytometers analyze and sort small particles and single cells in liquid suspension by detecting light scatter within (over) narrow cone or solid angles at various angles to the incident optical beam and fluorescence emission at various wavelengths. Information about cell size and structure can be derived from light scatter collected at different angles. For example, information about size can be derived from light scatter detected at low angles relative to the incident optical beam while information about internal cellular granularity can be derived from light scatter detected at a wide angle (near a right angle) relative to the optical beam. Further, the prior art shows that size of the granular structures to be detected determines the angle and acceptance cone for optimal wide-angle detection.

Light scatter signals collected at specific angles and over narrow cone angles are also used to gate detectors of weak fluorescence from single cells. Weak fluorescence signals cannot be effectively used to mark the presence of a cell in the optical beam because high levels of electronic noise accompany these signals. Noise spikes frequently exceed the threshold level for fluorescence detection and produce false readings that are confused as weakly fluorescing cells. To avoid this, flow cytometers generally use signals from one or more detectors situated to detect light scatter at one or more angles relative to the beam to produce relatively noise free signals that can effectively discriminate against false fluorescence from electronic noise, and gate true fluorescence from cells (see U.S. Pat. No. 4,284,412, incorporated herein by reference).

One key to the use of these light scatter detectors as fluorescence gates is using a narrow solid angle of detection. For example, so-called "low angle forward scatter" (LAFS) detectors are frequently placed as close as 0.5 degrees to the optical axis and collect light only within a one degree cone. Wide-angle light scatter detectors are frequently placed at positions ranging from approximately 10 degrees to 90 degrees off axis and also collect light within small cone angles of less than five degrees. If the cone angle of collection is not kept as small as possible, then information about granularity and size can become merged. Under these conditions for example, large cells become indistinguishable from small cells and granular cells become indistinguishable from non-granular cells of the same size.

When narrow acceptance cone light scatter (NACLS) detectors are used to monitor the passage of multicellular organisms such as *C. elegans*, three problems arise that do not occur with single cells such as blood cells. First, it is found that the light scatter signal does not necessarily rise above baseline (zero) at the beginning of the passage of the organism through the optical beam, but instead rises at an unpredictably later time. Second, it is found that the light scatter signal does not necessarily return to baseline (zero) at the end of the passage of the organism through the optical beam, but instead returns at an unpredictably early time. Third, it is also found that the light scatter signal frequently returns to baseline (zero) at one or more unpredictable times while the organism is in the beam.

Therefore, the most basic effort to size multicellular organisms based on their "time of flight" through the analysis light beam is thwarted by this unpredictable behavior of light scatter signals that are collected over narrow cone angles. Furthermore, the narrow cone angle light scatter signals that start late are not useful for gating fluorescence signals. Finally, the narrow cone angle light scatter signals that return to baseline early cannot be used to denote the position of fluorescence along the axis of the worm. The signals that return to baseline early can also be confused with the passage of two or more separate organisms when actually only one passed through the analysis beam.

The present invention does not employ the usual single cell, light scatter detection methods, and instead uses light scatter collection over very wide cone angles when analyzing and sorting multicellular organisms. One aspect of the invention is to collect scattered light over a wide cone angle such as 20 degrees or more. This provides a light scatter signal that becomes positive accurately at the time the organism enters the beam, remains unambiguously above baseline while the organism is in the beam, and returns to baseline accurately at the time the organism exits the beam. This aspect of the invention enables another aspect of the invention, which is to use accurate, unambiguous, light scatter signals collected over wide cone angles to mark the linear position of weak and noisy fluorescence signals along the axis of the organism. The width of the cone angle needed depends upon the type of organism.

In FIG. 14, and in the preceding paragraphs the fluorescence optical configuration is described. Additionally, a spatial filter and forward scatter detector are placed on the beam axis after the optical exit of the flow cell.

Gating Using Extinction: Optical Illumination/Detection Using Extinction

The present invention also provides a system having two lasers: a red (e.g., 635, 670 nm) diode laser that is used to measure the optical extinction (axial light loss) of the organisms and an excitation laser (e.g., a multine argon-ion laser, etc.). Optical extinction of red light provides a highly reliable "triggering" signal that indicates when the worm in passing across the light beam in front of the detector. The signal consistently rises above baseline as the organism enters the beam and does not return to baseline until the organism has left the beam. Use of a longer wavelength (red) light dramatically reduces the anomalous signals observed with using extinction with the argon ion laser beam. Another advantage provided by the red light is that the diode lasers generate far less background fluorescence or "noise," due to higher speed fluctuations in signal intensity compared to the argon ion lasers. This further improves the signal to noise ratio for the optical extinction detection.

In certain preferred embodiments, silicon photodetectors are used to measure the axial light loss signal. Of course, those skilled in the art will appreciate that other types of signal detectors can be used such as avalanche photodiodes, and photomultiplier tubes.

In FIG. 14, and in the preceding paragraphs, the fluorescence optical configuration is described. Additionally, in the extinction measurement configuration, an illumination laser (e.g. a diode laser) is combined and aligned coaxially with the fluorescence excitation beam (21, 22), the combined beams are then focused into the analysis zone of the flow cell. A long pass filter is placed in the extinction beam path to reject the excitation light from the excitation laser. In addition, an optical slit is placed in between the flow cell and the extinction detector, both located on the optical axis. The function of the slit is to allow the light attenuated by the organism to reach the detector, and rejects the forward scatter light from the organism. The slit has a collection angle of approximately 0.0 to 0.5–6.0 degrees in the horizontal axis and approximately 17 degrees in the vertical axis. The collection angle in the horizontal axis is dependent on the flow cell capillary diameter.

Fluid Mechanics

According to the present invention, the flow cell of the instrument is preferably rectangular with a square cross-section capillary measuring 250 µm on a side for use with *C. elegans*. The flow cell capillary is preferably 1000 µm on a side to accommodate embryos and first through second instar, *D. melanogaster* larvae. However, those skilled in the art will appreciate that a flow cell capillary can have a rectangular flow channel from 250 µm to 500 µm, to 1,000 µm or even 2,000 µm. A 250 µm wide rectangular flow channel is most useful for sorting nematodes such as *Caenorhabditis elegans*. A 500 µm wide rectangular flow channel is most useful for rapid sorting of *Drosophila melanogaster* embryos, although it can also be used to sort smaller model multicelluar organisms such as *C. elegans*. The 1,000 µm wide rectangular flow channel is most useful for sorting *Drosophila melanogaster* up through the second instar larva. Finally, the 2,000 µm wide rectangular flow channel is intended for larger model organisms such as third instar Drosophila larva, and zebrafish (*Danio rerio*) embryos and hatchlings. Sheath flow is used to orient these elongate organisms as they emerge from the sample nozzle and enter the flow cell capillary.

Figure 2:
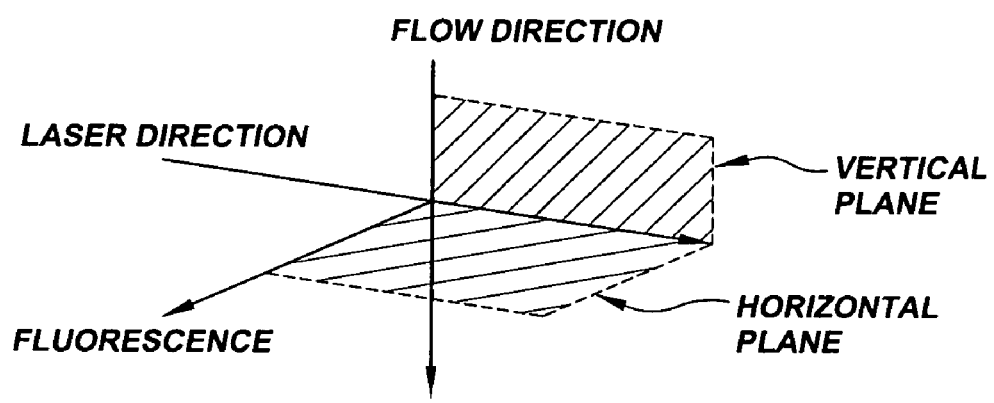
FIG. 2 shows a diagrammatic representation of the optical beams of the instrument of FIG. 1
Figure 13:
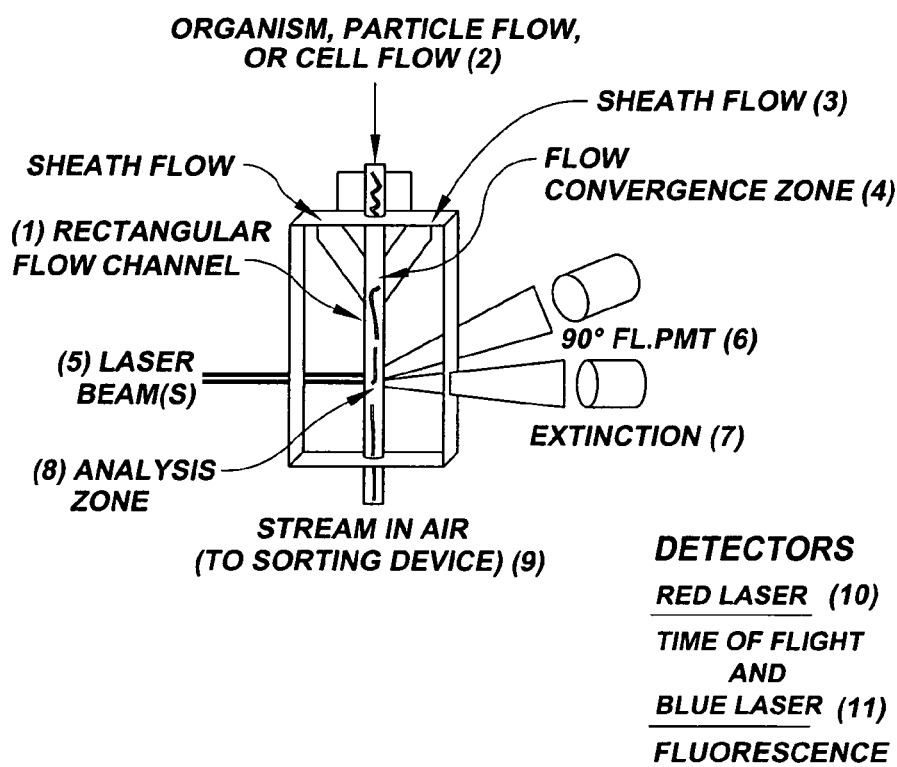
FIG. 13 illustrates the instrument of the invention that is a flow cytometer equipped to sort multicellular organisms based on spatially distinct, optically detectable, phenotypic characteristics.

This capillary flow cell is located at the line focus of the laser beam. FIG. 2 diagrammatically shows the geometric relationship of the flow and the various optical beams. The fluorescent light is collected by simple aspheric lenses or microscope objectives and passed through emission filters to photomultipliers. By virtue of the focused laser beam and the collection lenses, the flowing organism is optically scanned as it passes through the focus. FIG. 13 illustrates the instrument of the invention, which includes a rectangular flow channel (1) for through which to pass the organism, particle or cell (2). The sheath (3) flow intersects the rectangular flow channel (1) at the flow convergence zone (4). An aperture to supply an air stream to sort the organism is included (9).

Data Acquisition

There is theoretically no limit to the number of optical features that could be simultaneously monitored. The present invention can measure two, preferably three, more preferably four colors and many different features within each color. However, without limiting the invention, we propose that the number of signals, e.g., fluorescent features, can vary from 1–3, 1–4 1–10, 10–30, 30–50, or 50–100.

In preferred embodiments, the software on the user interface PC is the only interface between the user and the instrument. The customer is provided, e.g., with a "headless" Linux computer (a computer for which no monitor, keyboard, or mouse is provided and which is intended to prevent user intervention) in addition to the user interface PC. The "headless" PC would not allow user intervention and would in essence become a component of the instrument rather than an independent computer.

One particular profiler that has been used in the inventive system is an option comprised of a second, Linux PC and novel software. This software allows for analysis and sorting of animals based on their axial patterns. Axial pattern analysis can be performed on one signal (any color of fluorescence or axial light loss) selectable by the user. The present invention further provides simultaneous axial pattern analysis on two or more signals. There is no theoretical limit to the number of different signals that can be analyzed simultaneously, as described above for light scatter (WACLS) signals.

Signal Analysis

In certain preferred embodiments, the present invention uses the unambiguous light scatter signal from a wide acceptance angle, light scatter (WACLS), or light extinction (EXT) detector as a gate as well as a timing method for the analysis of fluorescence along the axis of the organism. The location of fluorescence along the axis of the organism is an important parameter for analysis and sorting. For example, with C. elegans, it is important in many applications to separate males from hermaphrodites. This can be accomplished with a fluorescently labeled lectin (wheat germ agglutinin) that binds to the vulva of the hermaphrodite and the copulatory bursa of the male. These two structures are not easily distinguishable in brightness, but the vulva is located near the midpoint of the organism and the copulatory bursa is located in the tail. Thus, axial location of fluorescence becomes the parameter for differentially analyzing and sorting males and hermaphrodites. This is illustrated schematically in FIG. 3 where two oscilloscope traces are shown for single organisms. One trace (panel A), has a fluorescent peak near the midpoint, and the other trace (panel B) has a fluorescent peak at the tail.

Figure 3A:
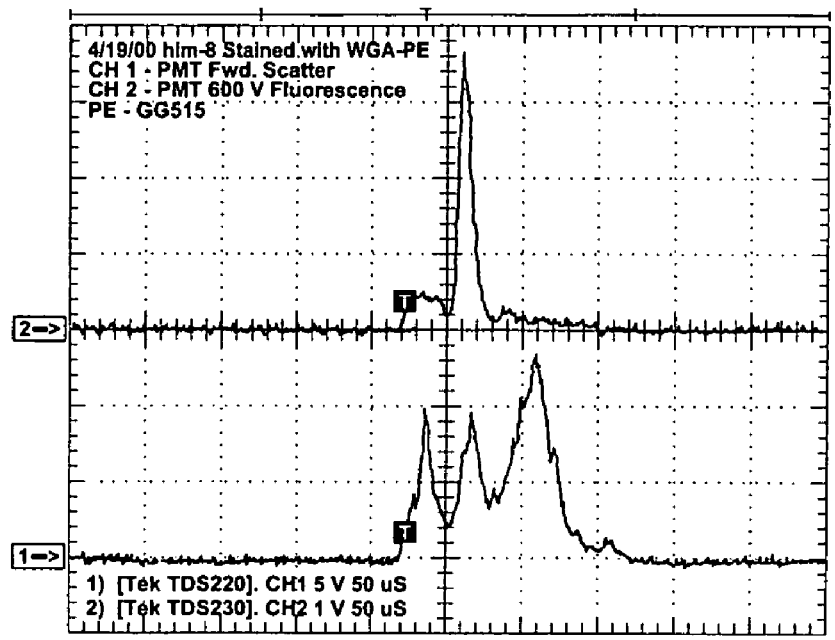
FIG. 3, panels A and B, show diagrams relating fluorescence signals (gated by one of the methods of the invention) related to hermaphroditic (panel 3A) and male (panel 3B) *C. elegans* as measured by the instrument of the present invention.
Figure 3B:
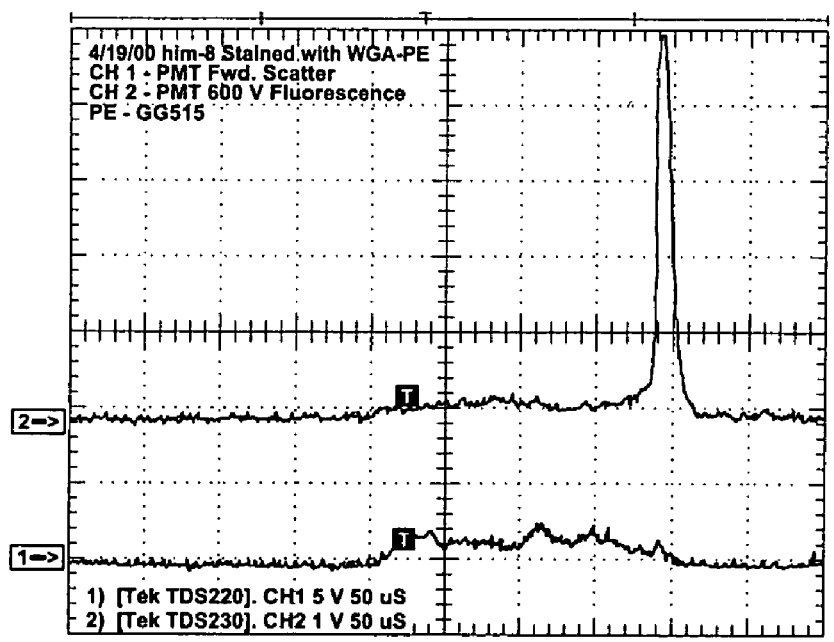

Since there is no fluorescent signal to mark the beginning of the organism in the oscilloscope traces of FIG. 3, a means must be established to mark the beginning and end of the passage of the organism through the light beam. This is done by the use of the wide acceptance cone light scatter (WACLS) signal. The start of this signal triggers a clock in the electronic processor that, in turn, causes fluorescent data to be sampled at regular intervals in time while the wide acceptance cone light scatter signal remains above a preset threshold level. Sampling stops when the WACLS signal drops below threshold, denoting the end of the organism.

The following is a parametric representation of a multicellular organism that can be employed through the use of a WACLS signal to gate the sampling of fluorescence along the organism's axis. Consider a WACLS detector that produces signal S1 and a timing mechanism that samples signals from all other detectors every T microseconds. Assume that there are other light scatter or light absorption detectors situated at various angular positions with respect to the analysis beam. Let the signals from these detectors be denoted by S2, S3, . . . Sn. Further assume that there are fluorescence detectors sensitive to various emission wavelengths producing signals F1, F2, F3 . . . Fn. The matrix below has columns of data for each detector and rows of data for each sampling interval.

|  | S1 | S2 | S3 | ... | Sn | F1 | F2 | F3 | ... | Fn |
|---|---|---|---|---|---|---|---|---|---|---|
| T1 | 0 | 0 | 0 |  | 0 | 0 | 0 | 0 |  | 0 |
| T2 | a1 | 0 | c1 |  | 0 | e2 | 0 | 0 |  | 0 |
| T3 | a2 | b2 | c2 |  | d3 | 0 | f3 | g3 |  | 0 |
| T4 | a3 | 0 | c3 |  | d4 | 0 | f4 | 0 |  | 0 |
| T5 | a4 | b4 | 0 |  | 0 | 0 | f5 | 0 |  | 0 |
| Tn−1 | an−1 | 0 | 0 |  | 0 | 0 | 0 | gn−1 |  | 0 |
| Tn | 0 | 0 | 0 |  | 0 | 0 | 0 | 0 |  | 0 |

The matrix example above shows a WACLS signal S1 with non-zero entries from time intervals T2 to Tn−1. This is the independent timing signal for all other detector channels. The other light scatter detectors S2 to Sn are not necessarily WACLS detectors, and therefore have zero values during the time T2 to Tn−1. The fluorescence feature with emission wavelength F1 is small and localized within interval T2. This represents a feature that can be used to mark the "tail" of the organism (see FIG. 3).

The fluorescence feature with emission wavelength F2 is not as small (along the axial direction) and occurs at a different location than the F1 feature. The relative location of the feature is established by reference to the timing initiated by the WACLS detector signal S1. In the present embodiment, if the velocity of the organism is known and the "tail" marker is used, then the absolute location of this feature can be determined as well. The fluorescence feature with emission wavelength F3 shows up in two small locations indicated in the WACLS timing sequence as T3 and Tn−1.

Each scanned organism can be represented by a parametric matrix of this kind. While not containing as much information as a microscope image of the organism, the data acquisition times for such matrices are of the order of one microseconds to 250 microseconds, depending on the length of the organism. This high speed is achieved because simple, fast photomultipliers collect the scattered light and no image is formed. In cytometers, images are usually stored by CCD cameras, which are inherently less sensitive than photomultipliers and therefore require more time to collect enough photons to form an image. Imaging times for fluorescence analysis of organisms such as C. elegans are of the order of 50 milliseconds, which is from 200 to 10,000 times slower than the time required to collect and store the parametric data described above. In the present embodiment, the sampling time and the speed of the organism determine the spatial resolution of the parametric method. For example, when the organism typically travels at about 500 cm/sec through the analysis beam, then for a five microsecond sampling time the spatial resolution is approximately 25 μm.

Multicellular Organisms

The present invention employs strong fluorescence markers that can be detected against the strong autofluorescence background and used to "bracket" a section of the signal (i.e., a specific lengthwise region of the organism) where the experimentally created feature is expected to appear and electronically process only this smaller amount of electronic data. This shortened processing task provides valuable processing time for other tasks such as commanding a sorter mechanism before the organism has time to flow beyond the sorter's deflection point. To obtain adequate resolution of axial features the height of the line focus beam must be substantially smaller than the length of the organism analyzed. In addition, the invention provides a means to reduce the variability of the auto fluorescence profile and improve the detection of the markers.

The cells of multicellular organisms like C. elegans and Drosophila melanogaster (unlike phytoplankton) develop in a reproducible and spatially organized way. This organization is governed by both intracellular and intercellular interactions that provide developing cells with "positional information." Since the spatial location of cells is highly conserved from generation to generation in species such as the fly D. melanogaster, and the nematode C. elegans, it is possible to express markers that will become stable features of a particular genetic strain of the organism. The present invention takes advantage of this to provide a high signal-to-background "map" of invariant locations along the length of the organism. These locations serve as positional markers to bracket and isolate segments of an axial profile for signal processing.

A strain exhibiting such a "map" (marker pattern) can then be used in a number of research protocols where experimental fluorescence markers are created in a pattern that is independent of the strain marker pattern. The strain marker pattern serves as a reference for the spatial position of the experimentally induced fluorescence markers. Further, the synchronous nature of the markers wherein a marker signal will be found at an expected point allows enhanced detection of the marker signals against background noise.

An example of establishing a fluorescent marker strain of C. elegans follows. The genetic manipulations described are well known to those of skill in the art. The invention comprises the use of these genetic constructs. First, one constructs an expression vector that carries a gene for a fluorescent protein, for example ZsYellow from ClonTech, Inc., under control of the egl-17 promoter sequence. Next, insertion of this construct into the organism's genome results in expression in the M4 neuron located in the anterior bulb of the pharynx. This expression commences soon after the organism hatches and persists through adulthood. This insertion also results in expression in vulval precursor cells as early as the late L2 larval stage and continuing at lower levels in the vulva of the adult hermaphrodite worm. This pattern of fluorescence expression will be carried as a stable characteristic of the strain resulting from the insertion of the construct into the genome. The fluorescent signal in the head provides the instrument with a means to determine the orientation of the animal while the signal at the vulva provides additional positional information as well as providing some information regarding developmental stage. The invention consists of producing a stable longitudinal pattern and using it as an aid in signal processing. A preferred method is to construct a strain of organism with stable fluorescent markers. The variety of promoters and other genetic constructs that can be employed to achieve this aim is almost limitless.

Generally, the marker fluorescence pattern and the experimentally induced fluorescence pattern will be detectable by different optical channels. That is, if the marker pattern is one of red fluorescence, it is often advantageous to design the experimental treatment (e.g., a screen of potential pharmaceuticals) to show function by producing localized green fluorescence (i.e., non-red fluorescence). In such a scheme, the instrument can be instructed to look for a specific optical pattern using the red fluorescence optics to determine the longitudinal orientation of the organism and to provide additional positional information. Because this signal pattern can be preprogrammed, analysis can be performed more rapidly than if a more complex and variable single color optical system were used. The instrument then compares features in the green fluorescence signal to the positional information in the red. This approach has the further advantage that if the various features of the organism are closely spaced they are more easily resolved if multiple fluorescence markers are used. In some cases a third or even more channels (colors) can be used. Alternatively, it is possible to use only a single optical and electronic channel for both patterns (marker pattern and experimental or test). This would be useful in a case in which a version of the instrument described in patent application Ser. No. 09/465,215 was employed that utilized only one set of fluorescence optics. It is simply a matter of balancing instrument complexity and cost against the value of the added information obtained.

The point of the invention is a detectable spatial pattern used for improving signal processing and generally serving as a "map" to pinpoint the location of detectable patterns created or altered by experimental treatments. This does not necessarily require that the genetic-manipulation be used to directly create a fluorescent marker pattern. Exogenous markers such as fluorescently labeled lectins, particles or antibodies can also be used to mark the location of features created by genetic manipulation or of existing structures, such as the vulva, to create a pattern useful for signal processing. That is, the created spatial pattern may not be optically detectable until after treatment with a ligand or with a histochemical process. For example, the promoter or other spatially oriented genetic control element may actually control local expression of an enzyme whose presence is made detectable by a histochemical procedure prior to flow cytometric analysis of the organisms. The detection may be by means of fluorescence or by light absorption or light scatter. Light absorption or scatter may be due to a ligand, a histochemically synthesized dye or compound (e.g. precipitation product of a histochemical such as diaminobenzidine or a tetrazolium salt). Also, a particularly dense deposit of a protein or other biomolecule or structure resulting from the genetic manipulation may also be detectable by light scatter or other optical methods. In some cases there may be a useful "inherent" or "latent" pattern within a strain of test organisms. In that case treatment with a lectin or antibody is all that is needed to make the pattern usable.

Since not all markers can be made arbitrarily strong, a means to reduce the effects of autofluorescence is also important. Organisms are not oriented in an azimuthal direction in this invention, but are oriented only along the axis of flow. Consequently, different cellular masses are stimulated into autofluorescence depending upon the azimuthal orientation with respect to the laser axis. In other words, there will be differences in the auto fluorescence profile for each organism that passes through the laser because each organism will be in a different azimuthal orientation (e.g., vulva toward laser or vulva turned away from laser). To compensate for this, a second wavelength band of autofluorescence that lies outside the experimentally created fluorescence band can be monitored, and subtracted from the total profile. Azimuthal variations in autofluorescence in the two different bands will correlate. Subtraction of the second wavelength band of autofluorescence decreases autofluorescence without significantly altering the measured fluorescence signal from the experimentally created marker. Subtraction reduces the variability in the autofluorescence profile from organism to organism.

Signal processing electronics can be configured to integrate fluorescence signals or to detect the peak of such signals. Integration is useful in reducing electronic noise or laser noise for a spatially diffuse feature, and peak detection is useful in pinpointing the location of a spatially sharp feature. A marker strain profile can be used to trigger different signal processing methods (e.g. integration or peak detection) depending on the nature of the experimentally created feature. For example, a given marker strain might produce five spaced-apart marker features along the length of the organism. These marker features are reasonably strong so that peak detection would work well. However, the experimentally induced marker appears between the third and the fourth marker and is fairly diffuse spatially. Therefore, the system could advantageously be programmed to switch from peak detection to integration after the third marker is detected. This would allow optimal detection of the experimentally induced marker. It is only with the use of the tailored marker pattern strains of the present invention that such switching of signal processing electronics becomes possible.

Creating A Marker Strain

A general approach to creating a marker strain of organisms is to genetically introduce a set of features that are readily detected by a flow cytometer. A simple approach is to produce features that can be directly detected by their fluorescence-for example by introducing a gene for a fluorescent protein. Any detectable pattern can be used, however. Enzyme patterns can be detected by histochemical reactions producing a colored or fluorescent product. Proteins can be overexpressed so as to be optically detectable. Other biological products such as fat globules, crystals or natural pigments can also serve to form an optically detectable pattern. The pattern could be antigenic and be detected by of antibodies, or the pattern could be carbohydrate-based and detectable by addition of lectins. The lectins and antibodies can be fluorescent, or can be linked to histochemically detectable molecules or optically detectable structures such as microspheres. Although in most instances it will be necessary to employ genetic manipulation to produce an optimal marker strain, some naturally occurring organisms or strains of organisms have cryptic marker features that can be revealed through the application or antibodies, histochemicals or other such methods.

In the case of genetic manipulation it is advantageous to select a promoter that will result in a desired spatial pattern of expression. An example of such a promoter is the egl-17 promoter of *C. elegans*. This promoter sequence, when inserted at the 5' end of a gene, will result in expression of the gene product (protein) in the M4 neuron and in vulval precursor cells of the organism. The positions of these cells are well characterized and are invariant in a wild-type (N2) background.

The gene controlled by the chosen promoter should encode a detectable product. An example of such a gene product is a fluorescent protein such as the DsRed gene (ClonTech, Inc.). As already mentioned, a large variety of other detection methods are available such as those involving enzymatic or antigenic properties. An advantage of a fluorescent protein is that the organism can be analyzed directly with no need for special incubations or other sample preparation.

Standard molecular genetic techniques are used to clone the promoter DNA sequence, the detectable protein gene sequence, and other DNA sequences required for optimal expression in the organism into an appropriate plasmid vector. For example, the present inventors and their associates have constructed a series of expression vectors in which a synthetic intron has been inserted at the 5' end and the *C. elegans* unc-54, a 3' UTR (untranslated region), has been inserted at the 3' end of each ClonTech Reef Coral Protein gene (AmCyan, ZsGreen, ZsYellow, DsRed, DsRed2, or AsRed). The egl-17 promoter sequence has been inserted upstream of the 5' synthetic intron in each of the expression vectors resulting in egl-17 expression plasmid constructs for each fluorescent protein.

The expression plasmid DNA is then inserted into the genome of the host organism. One method used for *C. elegans* entails microinjecting plasmid DNA into the gonad of young adult hermaphrodites and selecting progeny that express the detectable marker. Such animals generally carry the marker DNA as an unstable extrachromosomal array. Additional steps are required to cause the DNA to become integrated into a chromosome and to select the progeny bearing this integration. This is generally accomplished by mutagenizing the animals to introduce random double stranded breaks in chromosomal DNA. During the DNA repair process extrachromosomal sequences can become incorporated into a chromosome. $F_2$ progeny that have undergone such an incorporation event can be screened. $F_2$ homozygotes from such an integration event are identified based on their ability to transfer the marker DNA to 100 per cent of their progeny. It should be noted that other methods, including some that result in integration into a specific site in a chromosome can also be used. The point of the present invention is use of the pattern-marked organism as opposed to creation of such an organism.

Figure 10A:
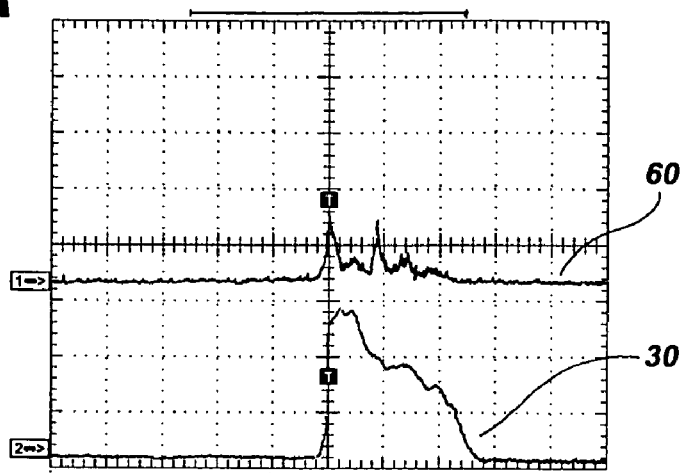
FIG. 10 shows oscilloscope tracings of optical detector signals resulting from flow cytometric analysis of *C. elegans* with panel A and panel B showing transgenic egl-17 expressing organisms corresponding to the organisms of FIG. 3 and panel C showing wild type *C. elegans* as a control.
Figure 10B:
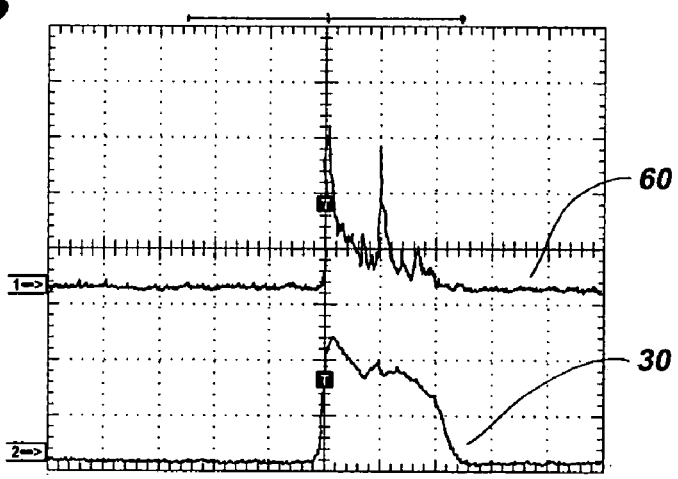
Figure 10C:
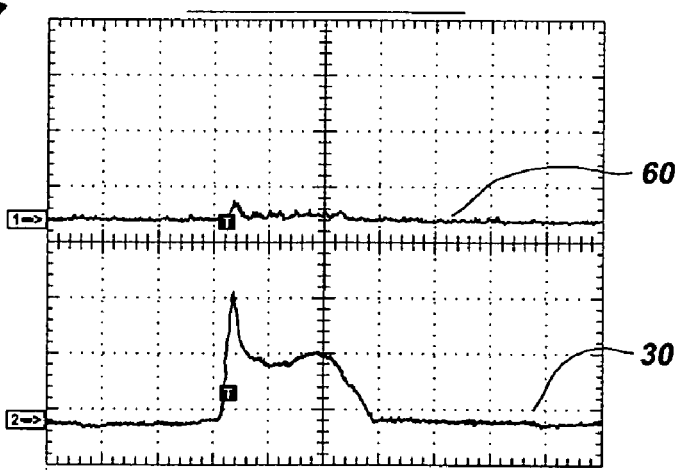

FIG. 9 shows photomicrographs of transgenic organisms where expression of a fluorescent protein is under the control of the egl-17 promoter. In this case the construct is egl-17::ZsYellow. FIGS. 9A and 9B show light micrographs of two organisms with FIGS. 9C and 9D showing the corresponding fluorescence images with the M4 head neuron (H) and vulva (V) marked. Diffuse autofluorescence of the gut is discernible between the head and vulva. FIG. 10 shows oscilloscope traces of the optical detector signal from flow cytometric analysis of these organisms. FIGS. 10A and 10B show oscilloscope traces from representative egl-17:: ZsYellow expressing *C. elegans*. An extinction signal 30 indicates when the organism enters and exits the laser beam. It should be understood that all references herein to extinction can be replaced by wide-angle forward light scatter or another signal shown to effectively indicate presence of an organism. The upper trace 60 represents yellow fluorescence. The yellow fluorescence signal 60 is indicative of the presence of ZsYellow and marks the head and vulva in the organism. These precisely located points of fluorescence represent a marker pattern as used in the present invention. These results should be compared with the trace (FIG. 10C) of a control organism lacking the genetic construct.

In cases where mutagenesis has been employed, it is advantageous to remove extraneous mutations by performing several rounds of mating with wild-type organisms and selecting for homozygotes for the inserted marker. Next, the marker must be transferred to an appropriate background strain for the planned assay by mating. For example, in a RAS pathway assay for new pharmaceuticals one could perform the screen using a C. elegans lin-15 mutant that already contains a second or possibly a third detectable marker. In that case the positional marker pattern generated above would be transferred by mating into the lin-15 strain. If only fluorescent markers were going to be utilized, one can simply mix the different DNAs prior to insertion into the genome thus simultaneously adding all markers into the appropriate strain. The desired background is one that shows an optically detectable response to an active compound. This allows the organisms to be used to screen compound libraries for drug candidates. The marker pattern ensures that the detected signal is positionally correct for the screened activity. That is, it is quite likely that test compounds may have multiple activities that could result in positional changes in the expressed signal and/or anomalous expression. The marker pattern allows the system to discriminate between positional shifts in expression. As explained below, the pattern is especially effective in enabling detection of weak signals resulting from test compounds.

Using Marker Pattern To Detect Suppression of a Disease Model Phenotype

Certain disease model pathways involve the inappropriate activation of gene expression in certain tissues or in the migration of certain cell types during development of the animal (which then results in positional changes in marker expression). One such model involves the Wnt signaling pathway in C. elegans. Components of this pathway appear to be conserved in other organisms and have been shown to function in the development of several forms of cancer, including breast cancer (Nusse, R., and Varmus, H. E., Cell (1982) 31, 99–109; Lejeune et al., Clin Cancer Res (1995) 1, 215–22) and colon cancer (Morin et al., Science (1997) 275, 1787–90; Rubinfeld et al., Science (1997) 275, 1790–2). Wnt signaling in C. elegans is involved in controlling the migration of specific cells (Korswagen et al. Nature (2000) in press). One example is that the proper migration of the QL neuroblast descendants depends upon the proper expression and function of the Wnt pathway genes mab-5 and egl-20 (Kenyon, C. Cell (1986) 46, 477–487; Salser, S. -J., and Kenyon, C., Nature (1992) 355, 255–8; Harris, J. et al. Development (1996) 122, 3117–31).

If the QL neuroblasts are marked with a fluorescent protein gene, the distance of these cells, which are normally located in the tail of the animal, from the vulva can be measured using marker pattern organisms. Note that the distance between the vulva signal and the M4 neuron signal in the pharynx allows for precise correction for the size of the animal and thus acts as an internal control. The disease model mutant displays inappropriate migration of these cells, or inappropriate expression of fluorescent protein in other cell types. In such a case, a high throughput drug discovery assay involves exposing the animals to compounds and determining which compounds caused the animals to assume a wild-type fluorescence pattern. The marker pattern enables the analysis to readily detect the shift of the positionally incorrect signal into a normal wild-type position. By allowing the signal analysis to focus on limited regions of the organism and/or by allowing a switching of the analysis mode (e.g., peak detection to integration) within specific (lineal) regions of the organism, the invention also allows the unambiguous detection of weak fluorescence signals.

Using Marker Patterns Recognition To Visualize Weak Signals

In some cases the autofluorescence (intrinsic fluorescence of the organism) signal of an organism is great enough to obscure the signal of a marker. In the case of C. elegans PY1089 GFP (Green Fluorescent Protein from Aequorea Victoria) is expressed in two adjacent neurons in the head of the animal. That fluorescence is visible under the microscope as two areas of more concentrated green fluorescence in a background of diffuse autofluorescence. Current automated analytical instrumentation integrate the total fluorescence signal of the organism and are therefore not sensitive to the brighter region within the autofluorescence. Attempts to resolve this strain from wild type C. elegans using such automated systems have been unsuccessful thus far. When the electronic signal from the organism is monitored a clear peak signal is seen at one end of the animal. By synchronizing the signal analysis to a known marker pattern, it is possible to determine the orientation of the animal (e.g., head first) and analyze only the specific GFP signal from the head neurons.

Figure 11A:
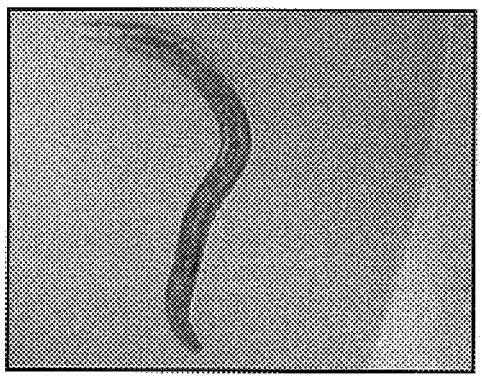
FIG. 11 shows PY1089 transgenic organisms expressing GFP (and showing autofluorescence) with panel A showing a light micrograph and panel B showing the corresponding fluorescence micrograph, while panel C and panel D show optical detector signals from these organisms undergoing flow analysis.
Figure 11B:
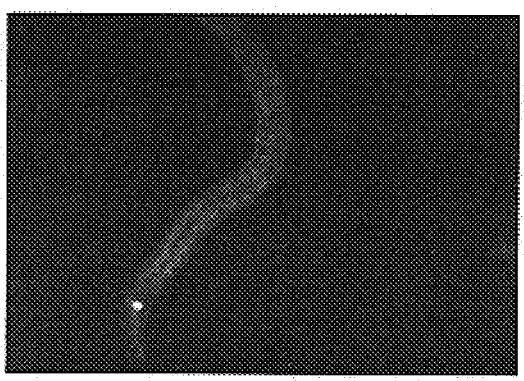
Figure 11C:
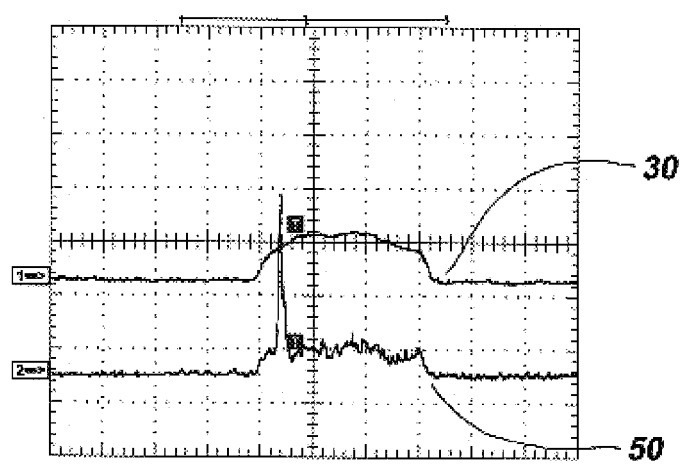
Figure 11D:
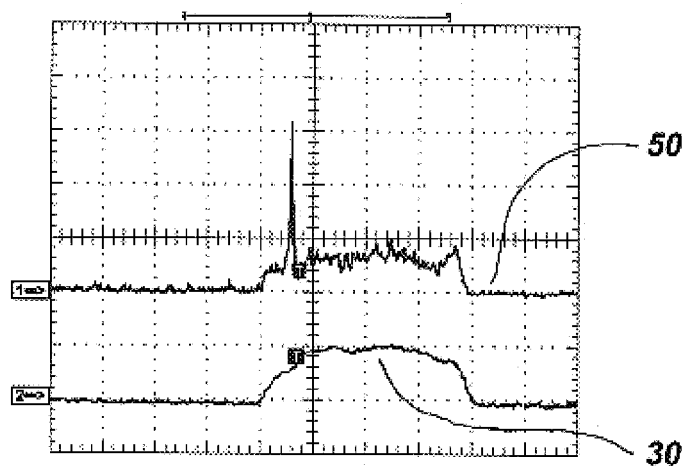

In the case of the animal whose oscilloscope traces are depicted in FIG. 11D, the total area under the fluorescence profile is 550 units while the area under the fluorescence peak is only 50 units resulting in a signal to noise ratio of 1:10. If, however, the area under the fluorescence peak is compared to an area of comparable width in the region of the animal with the highest autofluorescence that ratio changes to 2:1. If one then considers that the fluorescence signal from the two nerve cell bodies is 35 units, an assay is able to detect the presence of a third fluorescent cell body or the loss of one of the two fluorescent cell bodies.

A useful marker in this situation is the egl-17 positional markers described above. With egl-17::ZsYellow as the positional marker the instrument detects the M4 neuron in the anterior portion of the pharynx and the vulval precursor cells and rapidly determines the orientation of the animal as it passes through the analytical chamber. The software looks for the first green fluorescent peak immediately posterior to the M4 neuron and displays the intensity of only that signal. Results include signals such as 18 (no GFP fluorescence), 35 (GFP fluorescence in only one cell), 50 (fluorescence in two cells), 68 (3 cells), and 86 (4 cells).

FIG. 11 shows light and fluorescence photomicrographs of a C elegans PY1089 animal are shown in FIG. 11A and FIG. 11B, respectively. Oscilloscope traces depicting the optical detector signals generated by two different PY1089 animals are shown in FIG. 11C and FIG. 11D. In FIG. 11B the fluorescence from the head neurons (lower end of imaged organism) is clearly visible and is distinguishable from the overall autofluorescence of the animal. Here the animal is oriented such that the two neurons are aligned one on top of the other and only one slightly diffuse spot is observed.

In FIGS. 11C and 11D the one of the traces 30 shows the extinction signals from the animals while the other trace 50 show the green fluorescence signal. The animal in FIG. 11D was longer than the animal in FIG. 11C and was probably an adult. As expected, both the peak autofluorescence and the total autofluorescence (the area under the curve) are larger for the larger animal. The total fluorescence from the head neurons is approximately the same for both animals. For FIG. 11D the total area under the fluorescence curve is 542 units while the area under the GFP peak is 53. Of the peak area approximately 11.5 units are due to autofluorescence while the remaining 41.5 are due to the GFP fluorescence. These measurements indicate that discrimination could be made automatically provided that a marker pattern is available to automate decisions concerning the organism's orientation.

Figure 12:
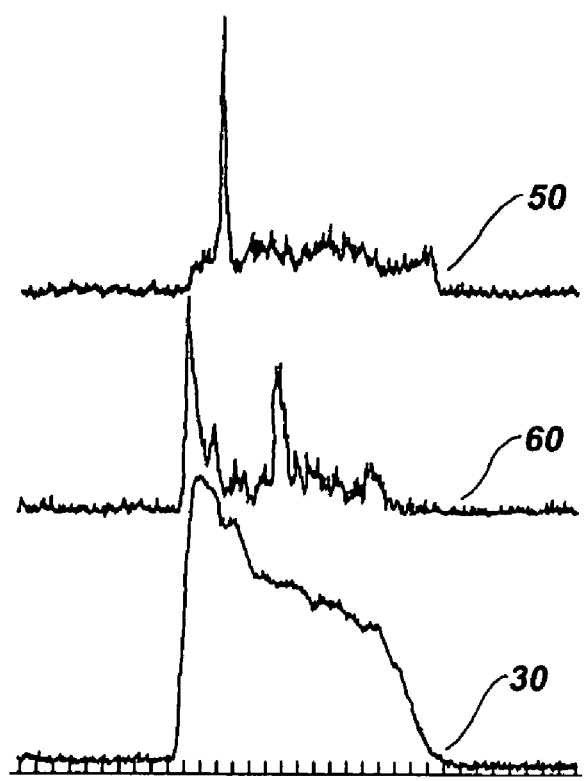
FIG. 12 shows optical detector signals that result from flow cytometric analysis of transgenic organisms resulting from mating the egl-17::ZsYellow construct into PY1089.

FIG. 12 is a graphic representation (oscilloscope) of the optical detector signals that would result from an egl-17::Zs Yellow construct mated into PY1089. The presence of an organism is determined by an extinction signal 30. A yellow fluorescence signal 60 (ZsYellow) clearly marks the head end of the organism (sharp spike used by the software to determine orientation) and provides several other fluorescence peaks along the length of the organism. A more diffuse green fluorescence signal 50 (GFP) is then integrated to determine the head neurons, which immediately follow the yellow M4 neuron peak.

The various marker patterns provided by the present invention allow the software to determine the orientation of elongate organisms, allow the software to specifically measure the position of treatment dependent signals (by comparison to invariant marker pattern signals), allow the software to alter the mode of signal analysis (e.g. peak detection versus signal integration) in a positionally controlled manner, and allow the software to limit detailed data analysis to specific positions along the length of the test organism. From the forgoing description a number of uses of the marker pattern organisms will be apparent to those of skill in the art. One method is to produce a test organism that expresses a marker pattern and also variably displays a detectable signal in response to one or more treatments. Generally a treatment will be exposure of the test organism to one or more test compounds, for example, to select active drug candidates from a synthesis library. However, the treatment may also include one or more environmental or other factors that potentiate or otherwise affect the action of the test compound. After the exposure to the treatment, the test organism is analyzed by a flow cytometer. The marker pattern is detected and the analytic software of the system uses the marker pattern to effectively analyze the signal that represents treatment response. As explained above, such analysis would be impossible or much less efficient without use of the marker pattern. It will be appreciated that a major goal is to select out organisms on the basis of their response to the treatment. This requires that data analysis be completed before the organism passes through the sorting section of the flow cytometer. Therefore, data analysis time is very brief and the enhanced analysis permitted by the use of marker patterns is often crucial.

The following description is provided to enable any person skilled in the art to make and use the invention and sets forth the best modes contemplated by the inventor of carrying out the invention. Various modifications, however, will remain readily apparent to those skilled in the art from a consideration of the specification or practice of the invention disclosed herein, since the general principles of the present invention have been defined herein specifically to provide optical gating devices and methods for use with an optical analyzer/sorter designed for elongated multicellular organisms and improved data processing of optical signals from elongate multicellular organisms by use of a pattern of markers of spaced apart along the long axis of the organisms. It is intended that the specification and examples be considered as exemplary only, with the true scope and spirit of the invention being indicated by the following claims.

EXAMPLES

Example 1

Simultaneous NACLS and Fluorescence From *C. elegans*

Figure 4:
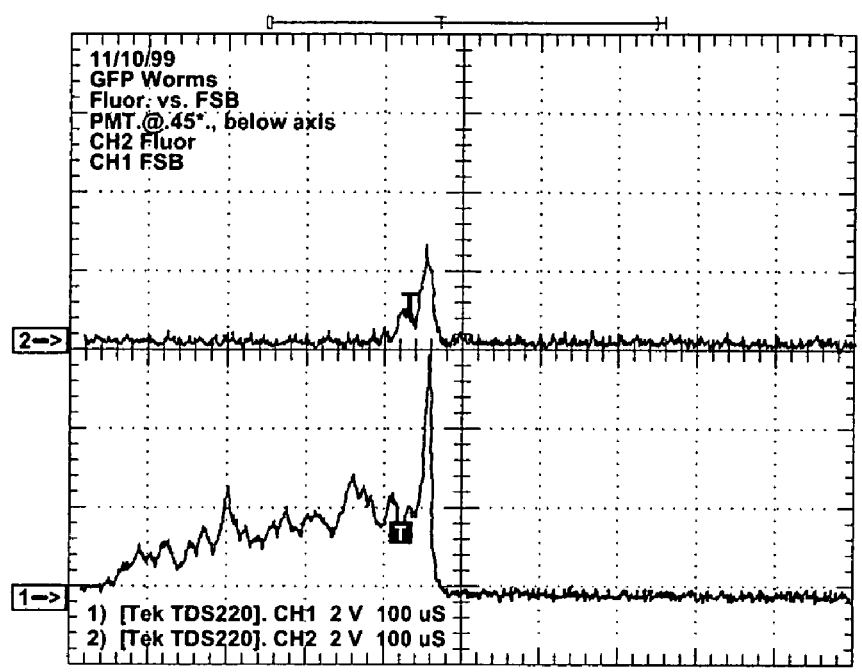
FIG. 4 shows actual oscilloscope traces from a NACLS forward light scatter detector (lower trace) placed at a 45 degree forward light scatter angle and fraction of a degree below the optical axis and a fluorescence detector (upper trace) at right angles to the optic axis.

A light scatter sensor was placed at various angular positions with respect to the optical axis in the forward scatter direction. The collection cone angle was approximately six degrees (NACLS). A photomultiplier with a 20×-collection lens and a barrier filter optimized for fluorescence from GFP was used on the fluorescence detector. The *C. elegans* that were used for this illustration expressed GFP at two locations in the "head" and nowhere else. The oscilloscope traces for light scatter and fluorescence are shown in FIGS. 4 and 5.

The traces show the passage of the organism through the line focus laser beam. The lower trace (1) is the light scatter signal and the top trace (2) is the fluorescence signal. The x-axis is time. FIG. 4 is typical of a class of light scatter traces observed with a NACLS detector. The detector was placed at a 45 degree forward light scatter angle directly below the laser beam axis (below the horizontal plane in FIG. 2) as it emerged from the flow cell. No scattered light from the flow cell structures themselves was incident on the detector. The NACLS signal appears to rise at the proper time. The onset of the NACLS trace and the weak autofluorescence trace from the anterior structures of the nematode coincide. The NACLS signal appears to return to baseline after the fluorescent head passes. Unfortunately, the trace returns to baseline approximately during the middle of the passage of the nematode as well. This would give the false impression that two organisms had passed rather than one. This NACLS signal demonstrates the need for a new, unambiguous trigger and timing signal.

Figure 5:
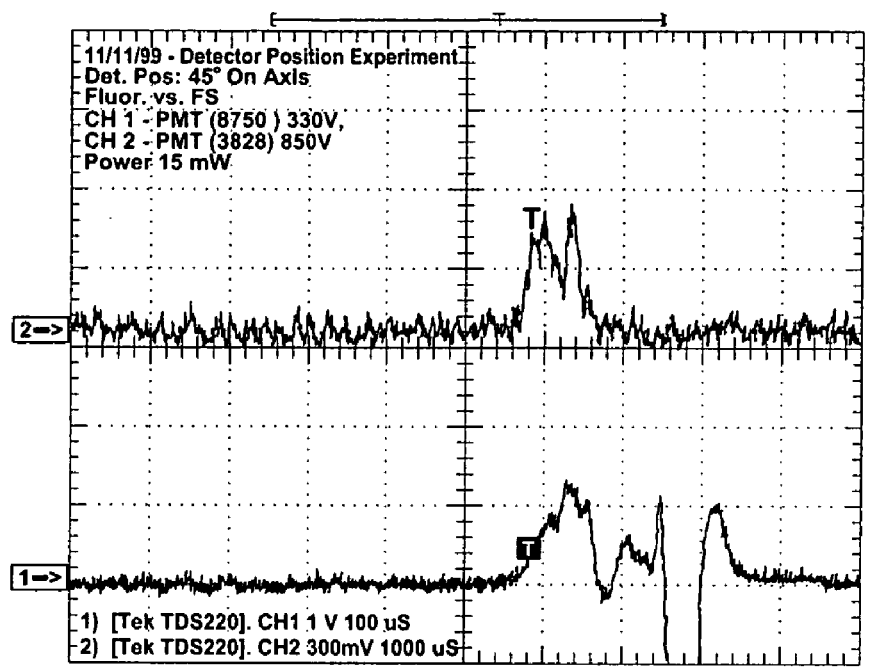
FIG. 5 shows actual oscilloscope traces from a NACLS forward light scatter detector (lower trace) placed at 45 degrees from the optical axis and a fluorescence detector (upper trace) at right angles to the optic axis.

FIG. 5 illustrates another problem associated with improper placement of a light scatter detector for triggering. In this example, the same detector was placed in the horizontal plane of FIG. 2, but at an angle of 45 degrees to the forward direction. In this case, stray, scattered light from the capillary was incident on the detector. A baseline restoration circuit was used to zero out this light level. The NACLS trace shows a false return to baseline that is caused by the acceptance cone angle being too small, and in fact the signal becomes negative. The negative signal is caused when stray light from the flow cell is blocked by the nematode to an extent that there is more light blockage than there is light scatter. (This signal could not be used as a trigger or timing signal for two reasons. The first reason is that the detector acceptance cone was too small and the second reason is that stray light on the detector became blocked by the passage of the nematode.)

Example 2

Figure 6:
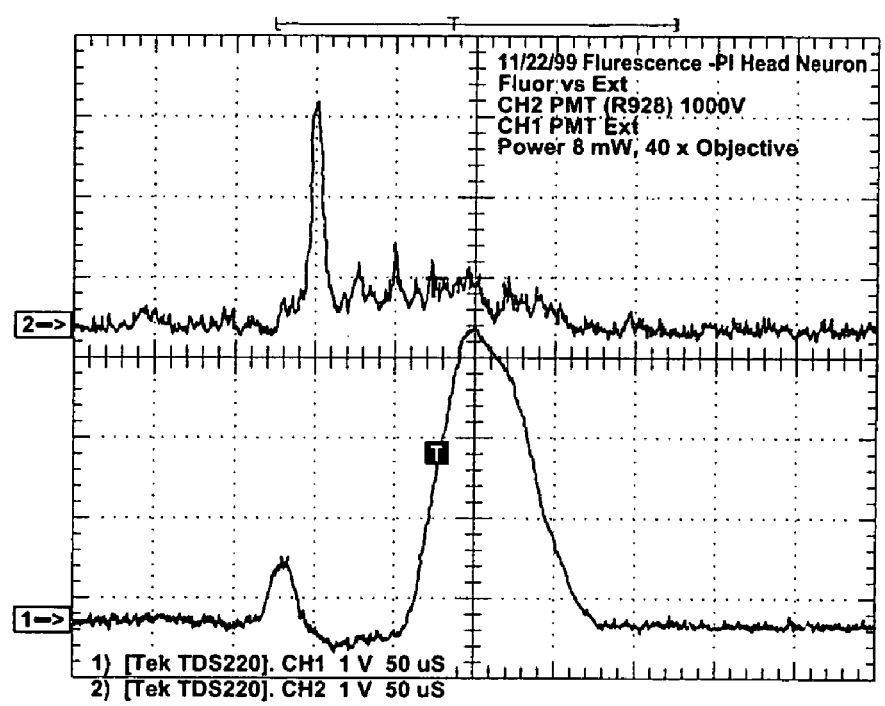
FIG. 6 shows actual oscilloscope traces from an extinction detector (lower trace) placed on the optical axis and a fluorescence detector at right angles to the optical axis (upper trace).

Problems Associated with Optical Extinction Signals as Trigger and Timing Signals FIG. 6 illustrates another problem associated with improper placement of a light scatter detector for triggering. In this case a sensor was place directly on axis and in the laser beam. The object was to measure light blockage (extinction) by the organisms. Light extinction is a possible alternative to the preferred WACLS (light scatter) trigger of the present invention. The test C. elegans had a single weak region of fluorescence at a neuronal location in the head located slightly posterior to the tip of the "nose." A 40×objective was used to collect more light since this organism was very weakly fluorescent. The extinction sensor collected light over a two degree cone. In this case, the extinction trace returns to baseline during the passage of the nematode, and even becomes slightly negative. Therefore, this signal could not be used as a trigger or timing signal.

Example 3

Simultaneous WACLS and Fluorescence from C. elegans

A photodetector was placed on the optic axis with a collection cone angle of approximately 30 degrees (WACLS). A mask was placed over the center front of the detector to block any directly transmitted light or stray scattered light from the flow cell capillary. This way, the detector collected light scatter from the organisms over a several times wider cone angle than in the previous examples. The photomultiplier with a 40×collection lens and a barrier filter for green fluorescence protein was used to detect fluorescence since the fluorescence signal was very weak.

Figure 7:
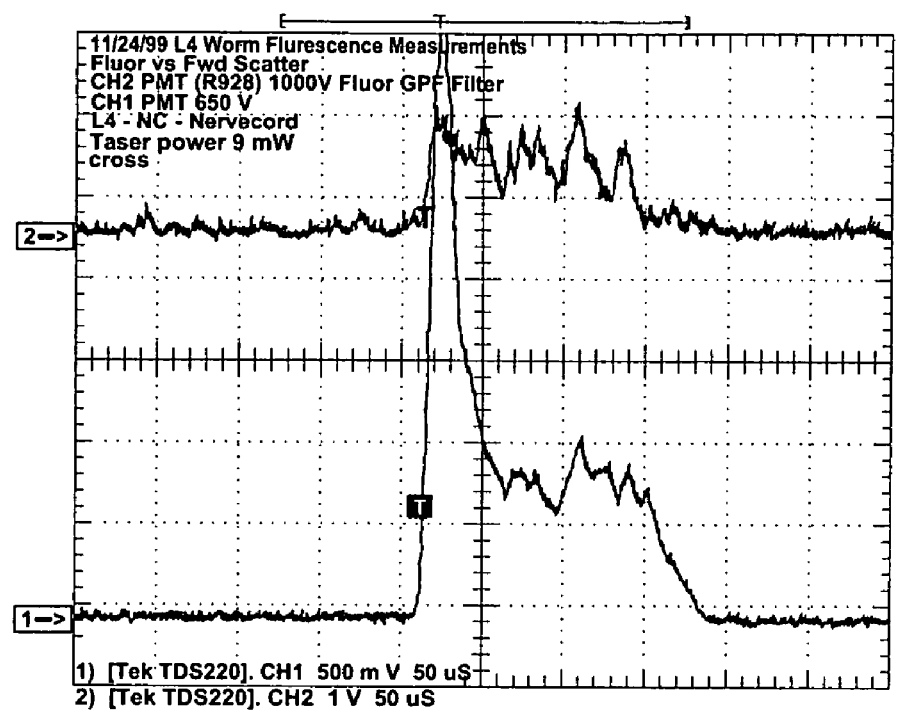
FIG. 7 shows actual oscilloscope traces from a WACLS forward light scatter detector (lower trace) and a fluorescence detector at right angles to the optical axis (upper trace); the *C. elegans* samples scanned showed several discreet points of fluorescence.

FIG. 7 shows a WACLS signal on the lower trace and the associated fluorescence signal on the upper trace. Note that the WACLS signal begins and ends at the proper time and does not return to baseline during the passage of the nematode. This was a consistent and systematic observation so long as the acceptance angle was sufficiently wide and light from the illuminating beam or the scatter detector did not collect stray light. The particular C. elegans used for this example expressed fluorescence along its entire length with 5 to 6 points along the axis where the expression was locally stronger. Some evidence for these local peaks can be seen in the fluorescence trace. The WACLS signal begins and ends at the proper time and does not return to baseline during the passage of the nematode through the laser beam. There were no exceptions to this observation when over 500 nematodes were analyzed. In the examples of useless trigger signals described above almost half of the signals returned to baseline improperly.

Figure 8:
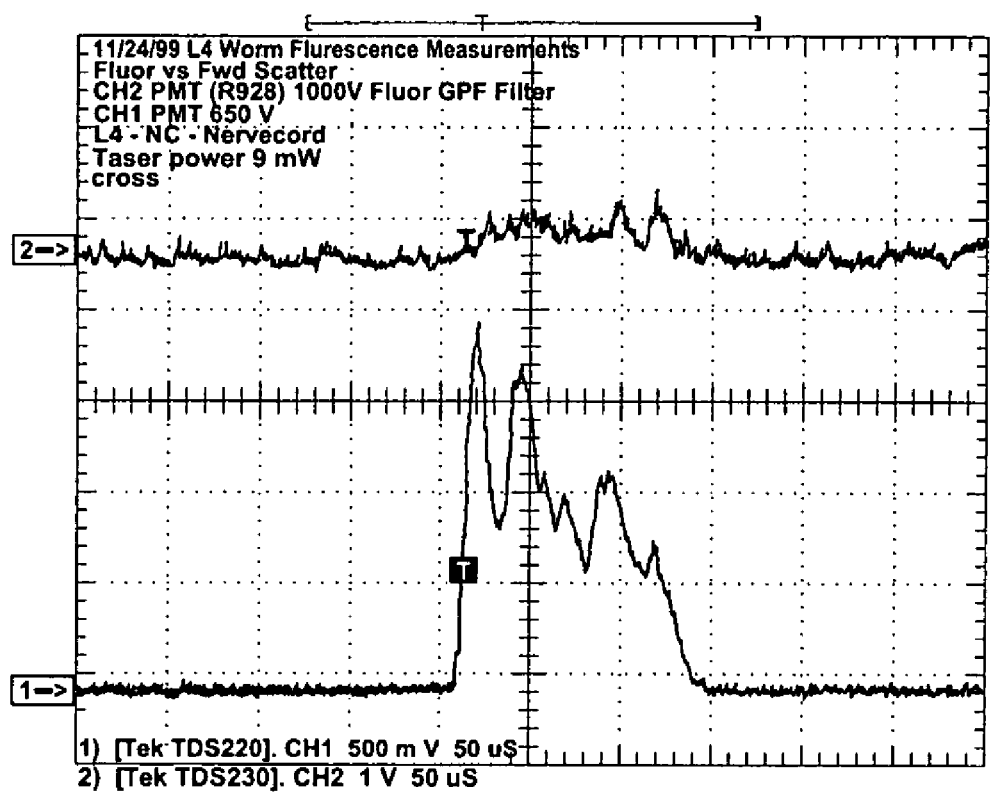
FIG. 8 shows actual oscilloscope traces from a WACLS forward light scatter detector (lower trace) and a fluorescence detector at right angles to the optical axis (upper trace); the *C. elegans* specimens scanned showed a small additional fluorescence at one end.

FIG. 8 also shows the traces for a C. elegans with very weak fluorescent protein expression. There is a low level of autofluorescence throughout the length of the organism and two local regions of weak expression near the tail. The WACLS signal begins and ends at the proper time and does not return to baseline during the passage of the nematode through the laser beam. The fluorescence signal is far too noisy to serve as a self trigger and timing signal, however the onset and end of the WACLS signal is strong and unambiguous, and could be used to time and guide an analysis of the fluorescence trace to the location of the two weak peaks.

Example 4

Detection of a Second Feature on C. elegans

Figure 16:
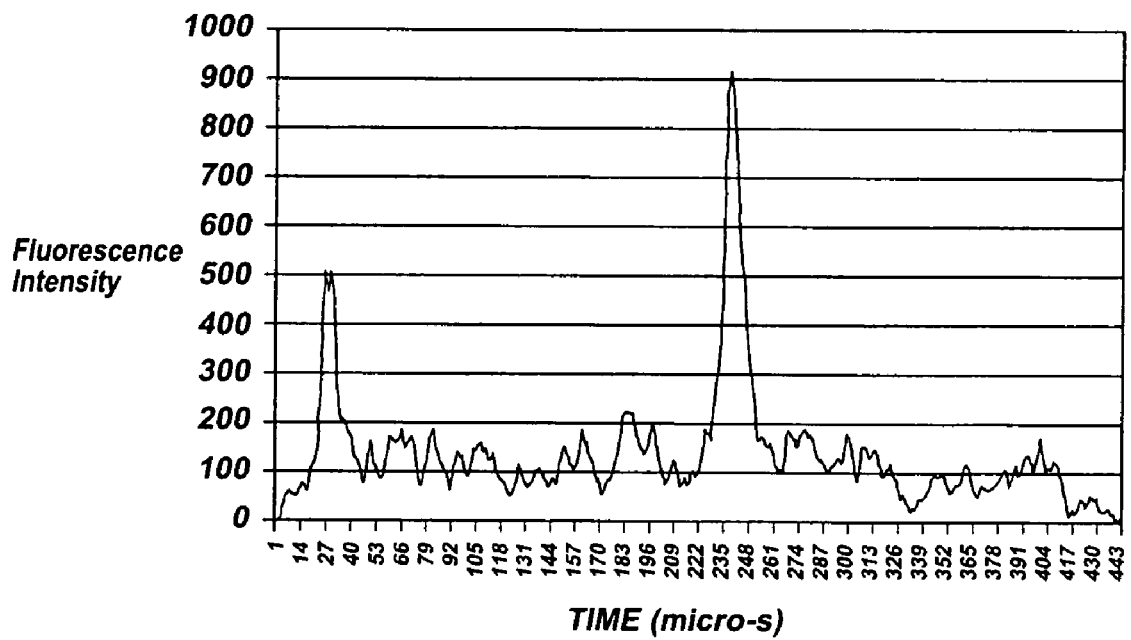
FIG. 16 is a graph showing a trace of a worm expressing the ZsYellow protein using the egl-17 *C. elegans* promoter. Expression is detected in one head neuron (left side of trace) and in the vulva (middle peak).
Figure 17:
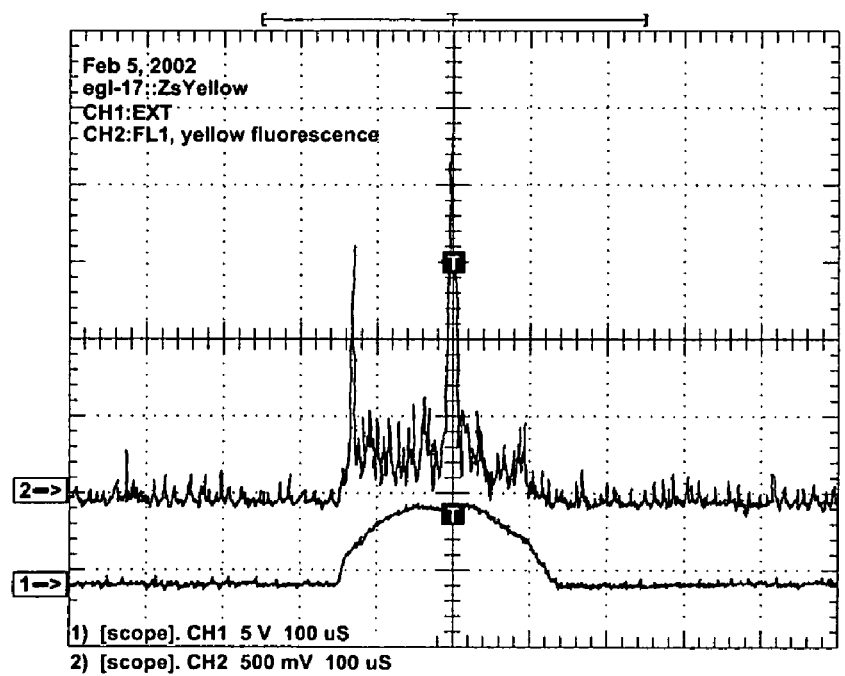
FIG. 17 is a graph showing a trace of a worm expressing the ZsYellow protein measured by an oscilloscope. The axial light loss signal is indicated by the lower trace and the yellow fluorescent signal is indicated by the upper trace.

FIGS. 16 and 17 show the signals generated from an individual transgenic C. elegans that expresses fluorescent protein (ZsYellow, ClonTech Corp.) in one head neuron and in the vulva. The trace in FIG. 16 is a graphic representation that shows the signal stored by the Profiler instrument. It is this data on which the Profiler sorting algorithms act. The ZsYellow protein is expressed using the egl-17 C. elegans promoter, which derives expression in one head neuron (left side of trace) and in the vulva (middle peak). This expression serves as marker pattern features to provide orientation and positional information.

FIG. 17 is a graphic representation of the same animal used to obtain the data for FIG. 16 that shows the unprocessed electronic signals generated by the animal as it passed through the laser beam. The lower trace in FIG. 17 shows the EXT (Axial Light Loss) signal that acts as a "triggering" parameter for the instrument. The upper trace shows the un-processed yellow fluorescence signal from the animal and is equivalent to the trace in FIG. 16. Both the EXT (trace 1) and the yellow fluorescence signal (trace 2) were obtained using an oscilloscope. This animal is an example of a marker organism that carries a stable longitudinal pattern that can be used as an aid in signal processing. In this case, the markers allow the software to distinguish head from tail (head neuron) and provide additional positional information (vulva).

Figure 18:
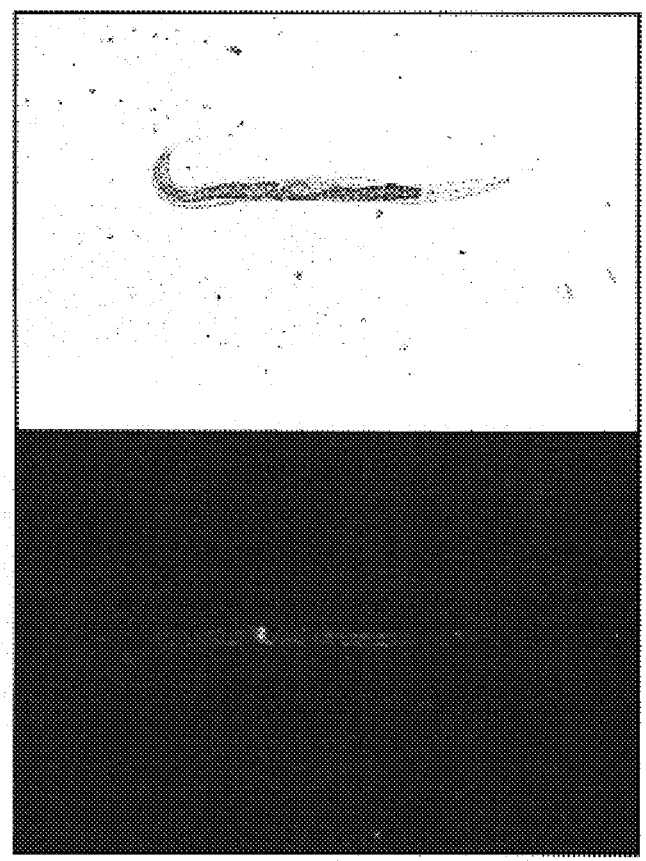
FIG. 18 is a photomicrograph of a transgenic *C. elegans* expressing ZsYellow under control of the egl-17 promoter. The upper panel shows a white light image and the lower panel is the corresponding fluorescence image. The fluorescent image has two bright spots corresponding to the vulva (middle) and the head (right) of the organism.

FIG. 18 is a photomicrograph of a transgenic C. elegans expressing ZsYellow under the control of the egl-17 promoter with the upper panel showing a white light image of the organism and the corresponding fluorescence image shown in the lower panel. There are two bright spots in the fluorescence image that correspond to ZsYellow fluorescence, one in the middle of the animal (vulva) and one small spot in the head of the animal (right side of the image).

Materials and Methods

The method used to create the organism depicted in the above images is described above. The method used to generate the traces in the first two panels was as follows. C. elegans were grown on agar media with a lawn of Escherichia coli. The plates were removed from the incubator (20-degrees C.) and flooded with a salts buffer. The liquid was gently swirled to lift the animals off the agar surface and the animals were transferred to a conical centrifuge tube. The animals were allowed to settle to the bottom of the tube and the buffer was aspirated to waste. The animals were resuspended in buffer and placed into a sample cup of the instrument at a concentration less than or equal to 1 per microliter. Sort parameters were set using the COPAS™ Profiler software on the user interface PC and using the Profiler software on the Linux PC. The sample was run by clicking the Acquire button followed by the Manual Sort button.

The following claims are thus to be understood to include what is specifically illustrated and described above, what is conceptually equivalent, what can be obviously substituted and also what incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A system for sorting multicellular organisms comprising:
   a population of multicellular organisms comprising a plurality of spatially distinct, optically detectable, phenotypic characteristics; and
   an instrument for detecting the location of the spatially distinct, optically detectable, phenotypic characteristic on the multicellular organism and for orienting the multicellular organism along its longitudinal axis.

2. The system of claim 1, wherein the spatially distinct, optically detectable, phenotypic characteristics comprise:
   a marker pattern, the marker pattern including a plurality of spatially consistent first features spaced apart along a length of each organism;
   and at least one second feature modifiable or inducible when the population is subjected to a test treatment.

3. The system of claim 1, wherein the instrument is a flow cytometer equipped to process elongate multicellular organisms.

4. The system of claim 1, wherein the instrument measures a gating signal for detecting the spatially distinct, optically detectable, phenotypic characteristic over background signals.

5. The system of claim 4, wherein the gating signal comprises light scattered in the forward direction.

6. The system of claim 4, wherein the gating signal comprises light attenuated by the organism in the forward direction.

7. The system of claim 1, wherein the instrument further comprises:
   a source containing multicellular organisms in a fluid suspension;
   means for causing the fluid suspension to move in a direction of flow;
   means for aligning the elongate multicellular organisms relative to the direction of flow;
   a light source for producing an optical beam through which the elongate multicellular organisms pass after becoming aligned;
   a first optical detector for detecting light over a solid angle of at least 20 degrees and over a collection angle of approximately 0.0 to 6.0 degrees in the horizontal axis and approximately 17 degrees in the vertical axis, for detecting passage of said organisms through said optical beam; and
   a fluid switch downstream of a point where said organisms pass through said optical beam, said switch responsive to the first optical detector to allow detected objects to pass to a sample container.

8. The system of claim 7, further comprising additional optical detectors for detecting sequential optical characteristics arrayed along a length of the multicellular organism wherein outputs of said detectors are gated by an output of the first optical detector to produce gated outputs.

9. The system of claim 8, further comprising a data representation of the sequential optical characteristics comprised of the outputs of the additional optical detectors.

10. The system of claim 9, further comprising a controller connected to the fluid switch and operative to cause said switch to select multicellular organisms showing data representations meeting predetermined criteria.

11. A method for sorting multicellular organisms comprising the steps of:
    providing a population of test organisms, wherein each member of the population displays at least one spatially distinct, optically detectable, phenotypic characteristic;
    analyzing the arrangement of spatially distinct, optically detectable, phenotypic characteristics of each population member; and
    depositing members of the population based on the arrangement of spatially distinct, optically detectable, phenotypic characteristics.

12. The method of claim 11, wherein the spatially distinct, optically detectable, phenotypic characteristics comprise:
    a marker pattern, the marker pattern including a plurality of spatially consistent first features spaced apart along a length of each organism;
    and at least one second feature modifiable or inducible when the population is subjected to a test treatment.

13. The method of claim 12, wherein the organisms are selected based on the location of the second feature with respect to the first features along the length of each organism.

14. The method of claim 12, wherein the organisms are deposited based on the location of the second feature with respect to the first features along the length of each organism.

* * * * *